US010694947B2

(12) United States Patent
Samzelius

(10) Patent No.: US 10,694,947 B2
(45) Date of Patent: Jun. 30, 2020

(54) SYSTEM AND METHOD FOR CONTINUOUS MONITORING OF CENTRAL NERVOUS SYSTEM DISEASES

(71) Applicant: Neurametrix, Inc., Hillsborough, CA (US)

(72) Inventor: Jan Samzelius, San Francisco, CA (US)

(73) Assignee: Neurametrix, Inc., Hillsborough, CA (US)

( * ) Notice: Subject to any disclaimer, the term of this patent is extended or adjusted under 35 U.S.C. 154(b) by 0 days.

(21) Appl. No.: 15/166,064

(22) Filed: May 26, 2016

(65) Prior Publication Data

US 2016/0345908 A1    Dec. 1, 2016

Related U.S. Application Data

(63) Continuation-in-part of application No. 14/318,477, filed on Jun. 27, 2014.
(Continued)

(51) Int. Cl.
    A61B 5/00    (2006.01)
    A61B 5/11    (2006.01)
    (Continued)

(52) U.S. Cl.
    CPC .......... *A61B 5/0022* (2013.01); *A61B 5/1118* (2013.01); *A61B 5/4088* (2013.01); *A61B 5/6897* (2013.01); *A61B 5/7275* (2013.01); *A61B 5/742* (2013.01); *G16H 15/00* (2018.01); *A61B 5/1124* (2013.01); *A61B 5/486* (2013.01); *A61B 5/7475* (2013.01); *G06F 21/316* (2013.01)

(58) Field of Classification Search
    None
    See application file for complete search history.

(56) References Cited

U.S. PATENT DOCUMENTS

| 4,805,222 A | 2/1989 | Young et al. |
| 5,557,686 A | 9/1996 | Brown |
| (Continued) | | |

FOREIGN PATENT DOCUMENTS

| WO | WO2007/078756 | 7/2007 |
| WO | WO2012/128952 | 9/2012 |

OTHER PUBLICATIONS

Frid et al.; *Analysis of Finger Tapping Parameters in People with ADHD*, dated 2012; IEEE 27th Convention of Electrical and Electronics Engineers in Israel (4 pgs.).
(Continued)

*Primary Examiner* — Sean P Dougherty
*Assistant Examiner* — Benjamin S Melhus
(74) *Attorney, Agent, or Firm* — DLA Piper LLP (US)

(57) ABSTRACT

A system and method for continuous monitoring of central nervous system diseases are provided in which typing cadence is used to measure cognitive function at a very granular level, providing hard, specific and detailed data to the neurologists about the central nervous system diseases. The system may also be used by a patient with a central nervous system disease to experiment with changes to diet, exercise and other things and test the effectiveness of those changes and patients can understand better why an unexpected improvement or worsening occurred.

12 Claims, 11 Drawing Sheets

Related U.S. Application Data

(60) Provisional application No. 62/167,766, filed on May 28, 2015.

(51) Int. Cl.
  *G16H 15/00* (2018.01)
  *G06F 21/31* (2013.01)

(56) References Cited

U.S. PATENT DOCUMENTS

| | | | | |
|---|---|---|---|---|
| 5,885,231 | A | * | 3/1999 | Cramer ................ A61B 5/1124 600/587 |
| 8,230,232 | B2 | | 7/2012 | Ahmed |
| 8,346,680 | B2 | | 1/2013 | Castleman et al. |
| 8,533,486 | B1 | | 9/2013 | Stark et al. |
| 8,997,191 | B1 | | 3/2015 | Stark et al. |
| 9,329,699 | B2 | | 5/2016 | Allen et al. |
| 2002/0192624 | A1 | | 12/2002 | Darby et al. |
| 2004/0059950 | A1 | | 3/2004 | Bender et al. |
| 2004/0167380 | A1 | * | 8/2004 | Simon ..................... A61B 5/16 600/300 |
| 2006/0195328 | A1 | | 8/2006 | Abraham et al. |
| 2007/0234056 | A1 | | 10/2007 | Mani et al. |
| 2008/0091639 | A1 | | 4/2008 | Davis et al. |
| 2008/0092209 | A1 | | 4/2008 | Davis et al. |
| 2008/0098456 | A1 | | 4/2008 | Alward et al. |
| 2009/0002178 | A1 | | 1/2009 | Guday et al. |
| 2012/0098750 | A1 | | 4/2012 | Allen et al. |
| 2012/0235819 | A1 | | 9/2012 | Watkins et al. |
| 2013/0176413 | A1 | | 7/2013 | Lowry et al. |
| 2013/0326604 | A1 | | 12/2013 | Hird |
| 2013/0338541 | A1 | | 12/2013 | Metman |
| 2013/0347099 | A1 | | 12/2013 | Smith |
| 2014/0058241 | A1 | | 2/2014 | Apparies et al. |
| 2015/0169854 | A1 | | 6/2015 | Chang et al. |
| 2015/0296023 | A1 | * | 10/2015 | Rokkaku ................ G06Q 50/24 709/203 |
| 2017/0116399 | A1 | | 4/2017 | Samzelius et al. |
| 2017/0116405 | A1 | | 4/2017 | Samzelius et al. |

OTHER PUBLICATIONS

Banerjee et al.; Biometric Authentication and Identification using keystroke Dynamics: A Survey; Journal of Pattern Recognition Research 7, 116-139 (2012).

H. Barghouthi; Keystroke Dynamics: How typing characteristics differ from one application to another; Masters Thesis: Master of Science in Information Security; Gjovik University College 67 pages (2009).

Clayton Epp et al.; Identifying emotional states using keystroke dynamics; Chi 2011 Session Emotional States 715-724 (2011).

Anil Jain et al.; Biometrics of Next Generation: An Overview: To Appear in Second Generation Biometrics' Springer 2010, 36 pages (2010).

Kevin Killourhy; A Scientific Understanding of Keystroke Dynamics: School of Computer Science Carnegie Mellon University: Thesis Committee: 213 pages (2012).

Kevin S. Killourhy et al. "Comparing Anomaly-Detection Algorithms for Keystroke Dynamics" Dependable Systems Laboratory, Computer Science Department, Carnegie Mellon University, 10 pages (2009).

Ryuhei Okuno et al. Finger Taps Movement Acceleration Measurement System for Quantitative Diagnosis of Parkinson's disease, Conference Proceedings . . . Annual International Conference of the IEEE Engineering in Medicine and Biology Society, 5 pages (Feb. 2006).

Information Security Stack Exchange; Authentication—Is behavioral analysis (e.g. keystroke dynamics) a reliable security mechanism for MFA? 5 pages (2013).

Signature and Keystroke Dynamics; Biometrics-The Hand-Signature and Keystroke Dynamics; 1 page (2013).

Esther Strauss et al. A Compendium of Neuropsychological Tests: Administration, Norms, and Commentary, Third Edition, Oxford University Press 1225 pages (2004).

J.R. Wall et al. "Can Motor Measures Tell us if Someone is trying? An Assessment of Sincerity of Effort in simulated malingering" Abstracts from the 18th Annual Meeting, 2 pages (1998).

Vizer, L. (2009) Detecting cognitive and physical stress through typing behavior. In Proceedings of ACM SIGCHI 2009 Conference on Human Factors in Computing Systems, Boston, MA 3113-3116, Apr. 2009.

Vizer et al. (2011). Detecting Cognitive impairment using keystroke and linguistic features of typed text: Toward an adaptive method for continuous monitoring of cognitive status. In Proceedings of Information Quality in e-Health—USAB 2011, Graz, Austria, Nov. 2011, A. Holzinger and K.M. Simonic Eds. Springer-Verlag, Lecture Notes in Computer Science 7058, 483-5000, 18 pages (2011).

Vizer, L. 2013. "Detecting cognitive impairment using keystroke and linguistic features of typed text. Toward an Adaptive Method for Continuous Monitoring of Cognitive Status",HFES 2013 Symposium on Human Factors and Ergonomics in Health Care: Advancing the Cause, 18 pages, (Mar. 2013).

\* cited by examiner

SYSTEM AND METHOD FOR CONTINUOUS MONITORING OF CENTRAL NERVOUS SYSTEM DISEASES

PRIORITY CLAIMS/RELATED APPLICATIONS

This application claims priority under 35 USC 120 and claims the benefit under 35 USC 119(e) to U.S. Provisional Patent Application Ser. No. 62/167,766, filed May 28, 2015 and entitled "System And Method For Continuous Monitoring Of Central Nervous System Diseases," and this application also claim priority under 35 USC 120 and a continuation in part of U.S. patent application Ser. No. 14/318,477, filed Jun. 27, 2014 and entitled "Neurological Disorder Determining And Monitoring System And Method," the entirety of both of which are incorporated herein by reference.

APPENDICES

Appendix A (14 pages) contains an example of a portion of the key action data stream for a particular user (serial number 1234); and Appendix B (1 page) contains an example of a piece of text that was typed by a user that generated the portion of the key action data stream shown in Appendix A.

Appendix A and Appendix B are part of the specification and are incorporated herein by reference.

FIELD

The disclosure relates generally to a system and method for monitoring a central nervous system disease.

BACKGROUND

Neurologists have for a long time tried to help patients with any one of a myriad of central nervous system (CNS) diseases, such as Alzheimer's, Parkinson's, MS, Hunting-ton's and ALS. Their problem has been never having a way to measure whether what they prescribed worked. For example, blood test measures are typically not affected by changes in cognition. The cognitive tests that may be used produce data which does not have the superior specificity these diseases require. The remaining test, Finger Tapping is analogous, but can only produce limited data.

The field of neurology have for many years sought a way to measure what they cannot generally observe—a living brain. However, neurologists today lack adequate and precise tools to help patients manage their Central Nervous System ("CNS") diseases. Doctors cannot obtain sufficiently granular, specific and objective measures to evaluate changes in medication regimen, diet or other treatment options. It is desirable to provide a system that provides continuous monitoring of CNS diseases.

DETAILED DESCRIPTION OF ONE OR MORE EMBODIMENTS

The disclosure is particularly applicable to the continuous monitoring of CNS diseases using the implementation of the typing cadence system described below and it is in this context that the disclosure will be described. It will be appreciated, however, that the system and method has greater utility since the continuous monitoring of CNS diseases may be implemented using other implementations of the typing cadence system that are within the scope of the disclosure.

The system and method for the continuous monitoring of CNS diseases using typing cadence provides monitoring so that the performance of the brain in terms of consistency can be measured objectively, precisely and at incredibly granularity. The system and method uses typing cadence (TC) which is a very strong habit. Research has shown that it is one of our strongest habits and habits are hardwired in the brain and when the brain is attacked by disease, the hardwiring begins to break, but it breaks slowly and in small increments which are not visible to a clinic, but visible using the continuous monitoring of CNS diseases using typing cadence. TC also produces lots of data, can easily be based on natural behavior, not test and is extremely user friendly to administer. Now, an implementation of a system for detecting and monitoring a neurological disorder that may be part of the system and method for continuously monitoring CNS diseases is described.

Figure 1:
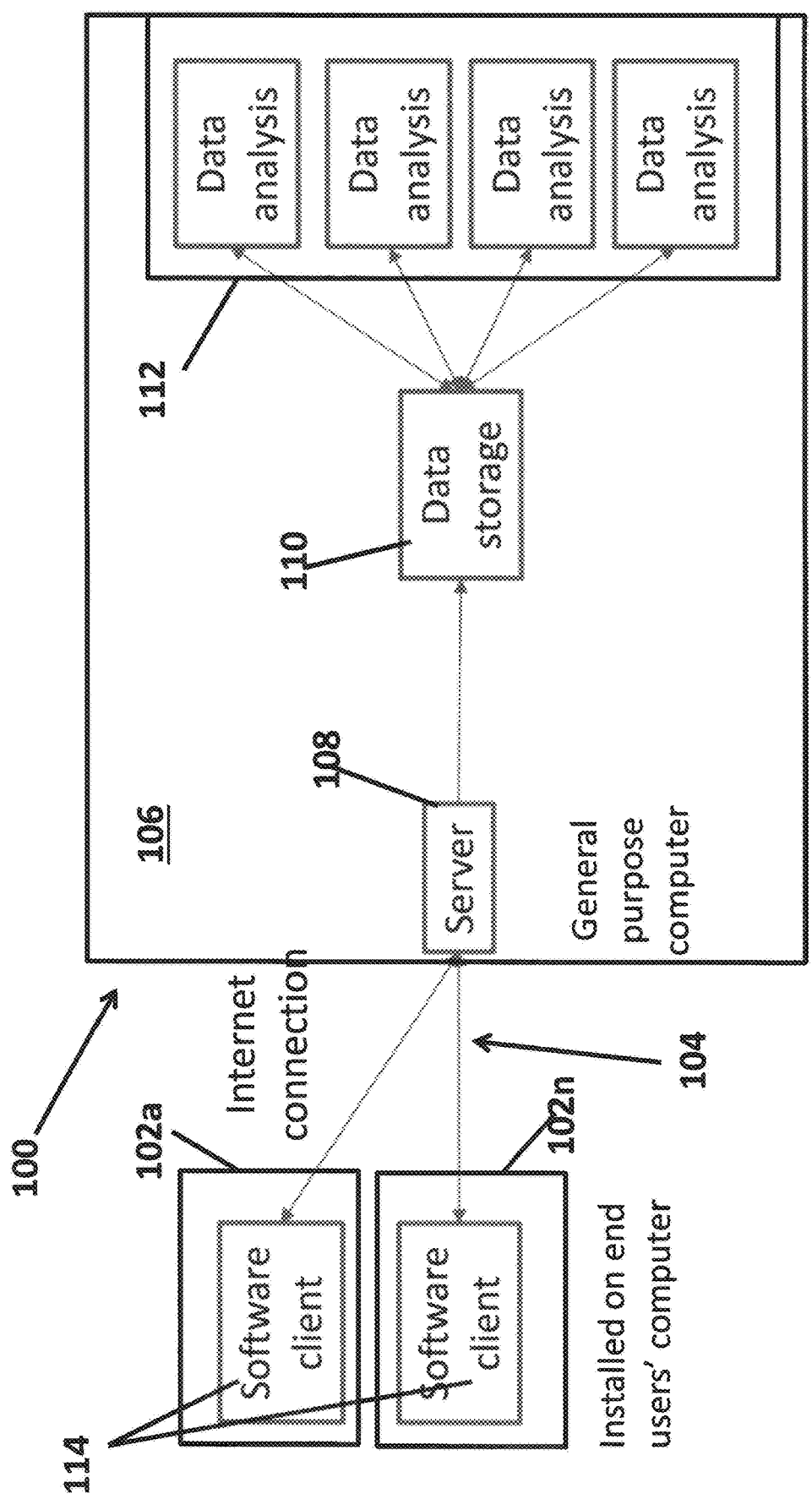
FIG. 1 illustrates an example of an implementation of a system for detecting and monitoring a neurological disorder.

FIG. 1 illustrates an example of an implementation of a system 100 for detecting and monitoring a neurological disorder. The system shown in FIG. 1 is implemented using a client server architecture, but the system may also be implemented as a cloud computing architecture, a standalone computer architecture or a software as a service (SaaS) model in which the typing cadence component, for example, may be downloaded to each computing device as needed. The system 100 may have one or more computing devices 102, such as computing device 102a, . . . , computing device 102n, each of which are connect to and communicate over a communications path 104 with a backend component 106. Each computing device 102 gathers, stores and communicates typing cadence data about a user who uses the computing device and the typing cadence data is sent over the communications path 104 to the backend 5 component 106 that receives, stores and analyzes the typing cadence data to detect symptoms of a neurological disorder.

Each computing device may be a processor based system that has some input device so that the computing device is capable of collecting typing cadence data from the user as the user performs his daily tasks that includes typing on the input device. For example, each computing device may be a desktop computer, a laptop computer, a tablet computer, a smartphone, such as an Apple iPhone product or an Android Operating system (OS) based device, or a traditional mobile phone. The input devices for each computing device may include, for example, a built in keyboard, a detachable keyboard, a glass surface, a touchscreen, a virtual keyboard, a keypad, an electronically generated keyboard on a touchscreen and the like. Alternatively, each computing device may be a standalone device that captures typing cadence of a user. Each computing device may also have a typing cadence component 114 that may be resident on each computing device. The typing cadence component 114 may be a hardware circuit, a piece of software code, a hardware circuit programmed with a plurality of lines of computer code or an application. In the case of the typing cadence component 114 having software code or computer code, the typing cadence component 114 may be stored in a memory of the computing device and may be executed by a processor of the computing device 102.

The communications path 104 may be, as shown in FIG. 1, a public internet connection or a private network connection. Each computing device 102 may connect to the communications path using a known protocol and then connect to another system, such as the backend component and communicate with the backend component using a known protocol that may or may not be secure. For example, the communications path 104 may be a computer network, the Ethernet, the Internet, a digital data network, a wireless digital data network and the like. In one implementation, the communication path between each computing device and the backend component may be a standard internet connection (secure or public) while the communication path between the front end components 108 and the storage units 110 may be implemented using a dedicated, private connection.

The backend component 106 may include one or more front end components 108, one or more data stores 110 and one or more data analytics components 112 that are connected to each other as shown in FIG. 1. These components of the backend component may be implemented in hardware or software or a combination of hardware and software. In one implementation, the components are implemented in computing resources, such as one or more server computers or one or more cloud computing resources that have at least a processor and a memory. In that implementation, each component may include a plurality of lines of computer code that may be stored in the memory and executed by the processor to provide the functions of each component that are described in more detail below with reference to FIG. 3.

In operation in one implementation, every user, patient or control, has the typing cadence component 114 installed on their computing device 102. The typing cadence component 114 hooks into the operating system and taps into the data stream from the input device and copies the clock time data for each key action/event. Each key action/event may be a the pressing of a key (key press) or a releasing of the key (a key release.) The typing cadence component 114 can store this information on the user's hard drive, but to greatly enhance security, the preferred embodiment is to store the data temporarily in a RAM of the computing device. The typing cadence component 114 may intermittently process the data, calculate all the differential timings used later in the process and packages a file it sends to the backend component 106. When the differential timings are calculated, as a security measure in some embodiments, the original clock stamps are removed—thus, the order of the characters is removed, making it impossible to put the data back to the original text.

An example of the key action data stream sent to the backend component 106 is contained in Appendix A that is incorporated herein by reference. Appendix A contains an example of a portion of the key action data stream for a particular user (serial number 1234.) As shown in the Appendix, the data may include first key identification data and second key identification data.

Thus, for example "8" represents a particular key being pressed or released while "76" represents another key being pressed or released by the user. In one embodiment, the value for each key that identifies the key may be the well-known ASCII value for the particular key. The data also has one or more time samples (TS1, TS2, . . . , TS10, etc) that each happen during a time interval when and after the key combination action occurs. In one embodiment, each 5 time sample may be measured in milliseconds. Each row in the data (other than the header row) represents a particular combination of first and second key actions and then time samples relevant to that particular combination of first and second key actions. When a particular row does not values for each sample period, the particular combination of first and second key actions has ended and no further key action data about that particular combination of first and second keys is available.

In the key action data in Appendix A, when the first and second key identifier are the same (such as in the first row), then the key action data represents a dwell time for the particular key (such as the key represented by the value "8") which is a time between a key press of the key and a release of the key by the user. As shown in the portion of the data, there are many different time samples for the dwell time for the key. In the key action data in Appendix A, when the first and second key identifier are different (such as "20" and "8" in the second row), then the key action data represents a flight time between a key press of the first key and a key press of the second key. As shown in the portion of the data, there are often fewer time samples for the flight time between the keys. The system may also detect a key event that is a key being pushed down or released by the user. Thus, a dwell time may be determined. The dwell time is a time period between when a given key is being pushed down (pressed by the user) and that same key is released by the user. Thus, the system and method may detect and use both flight time and dwell time. Thus, the typical cadence data from each computing device (and hence each user who uses that computing device) is captured and processed and used to, among other things, detect a possible neurological disorder of each user of each computing device. For example, the system may gather typing cadence data from users who do not have a neurological disorder and thus can compare the typing cadence data for a person without any neurological disorder to other users.

In operation, the backend component 106 may act as an organizer and may unpack the data file for each computing device, may determine to which user the particular computing device relates based on the file header of the particular data file, may convert the data from the format it was sent in into a common format, may calculate the profile data for the particular patient and may place the data and profile in the right folder in the data storage.

Figure 2:
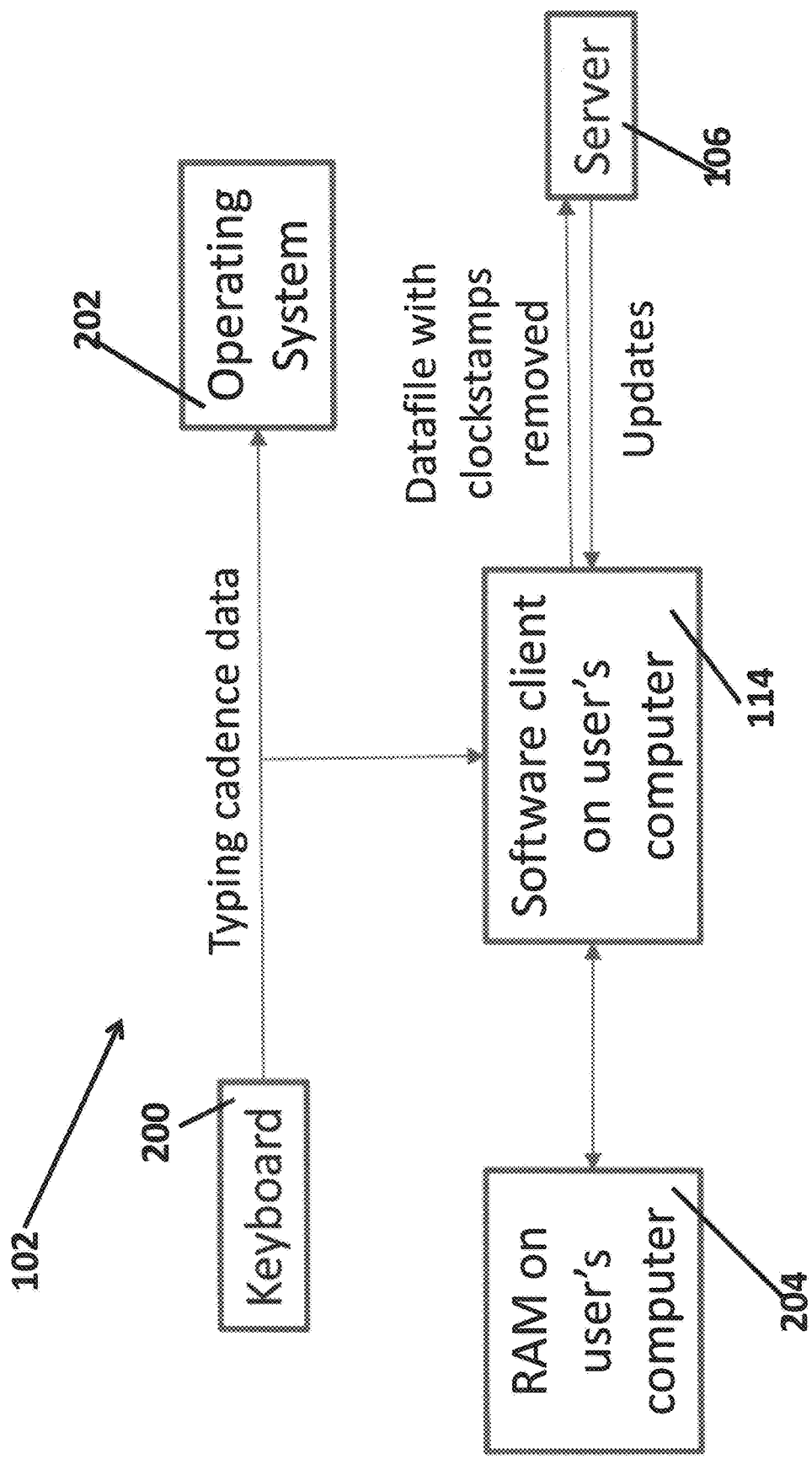
FIG. 2 illustrates an example of an implementation of a computing device that is part of the system for detecting and monitoring a neurological disorder.

FIG. 2 illustrates an example of an implementation of a computing device 102 that is part of the system for detecting and monitoring a neurological disorder. Each computing device 102 may include an input device 200, such as the keyboard as shown in FIG. 2, an operating system 202, memory 204, such as RAM in the computing device and the typing cadence component 114. The operating system 202 may include, for example, an Apple OS operating system for computers, a UNIX or UNIX like operating system, a Microsoft Windows operating system, an Apple iOS mobile operating system, the Android operating system and/or other tablet and smartphone operating systems. In operation as 10 shown in FIG. 2, the user may user the input device to type and the typing cadence component 114 (in combination with the operating system 202) may gather data about the typing of the user as well as the typing cadence data of the user which are sent to the typing cadence component 114. The typing cadence component 114 may then store the typing cadence data for a period of time and then sent a datafile with the clockstamps removed (as described above) to the backend component 106. The typing cadence component 114 may also receive updates from the backend component 106. The updates may include, for example, how many characters the typing cadence component on each computing device will record prior to sending a data file, a particular time of day that the client should stop and send a data file, etc. Appendix B contains an example of a document that was entered by a user using an input device and Appendix A is an example of a portion of the key action data stream that is generated based on the document in Appendix B being typed by a particular user.

Figure 3:
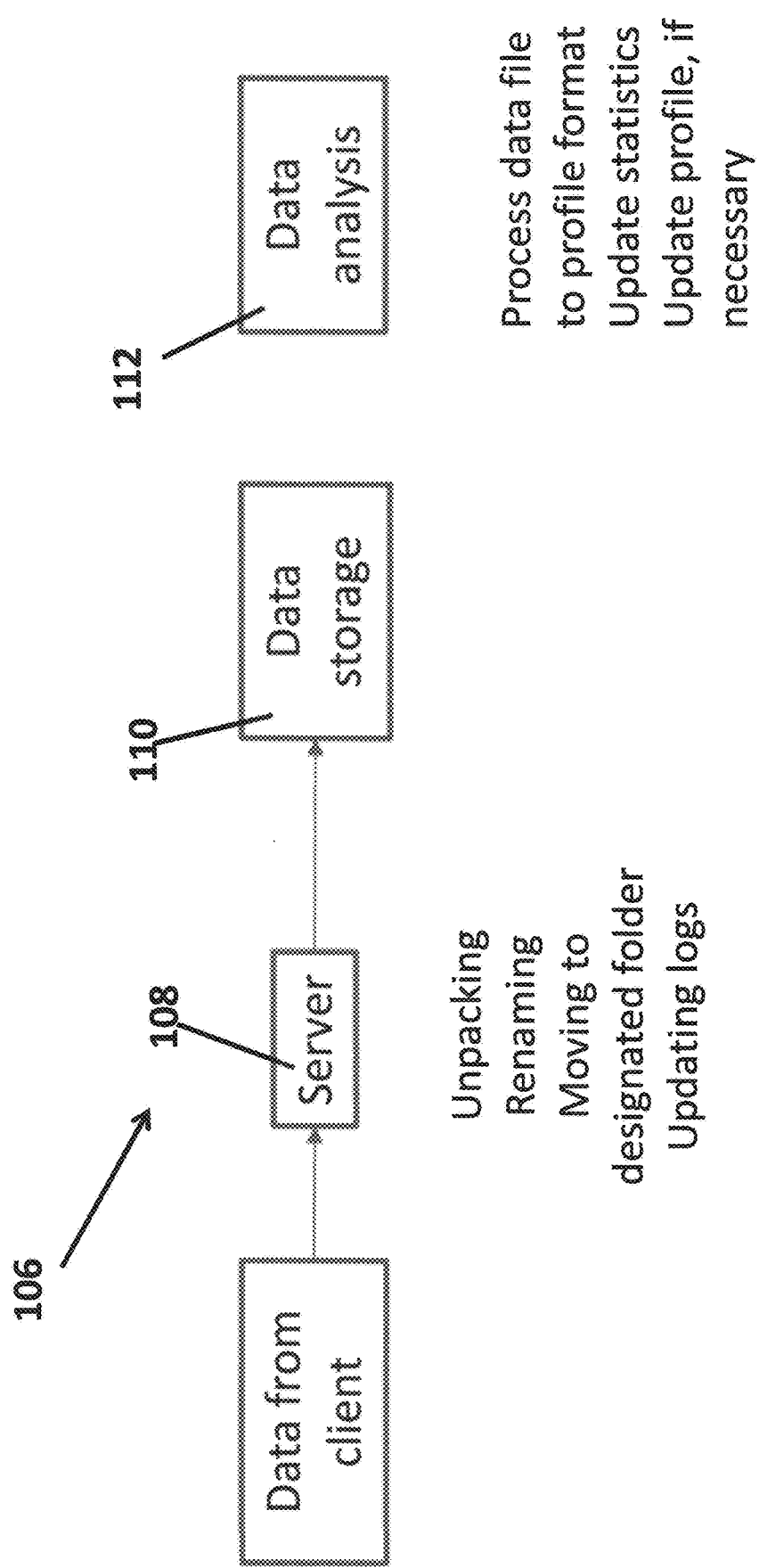
FIG. 3 illustrates an example of an implementation of a backend component that is part of the system for detecting and monitoring a neurological disorder.

FIG. 3 illustrates an example of an implementation of a backend component 106 that is part of the system for detecting and monitoring a neurological disorder. The backend component 106 may have the one or more front end components 108, one or more data stores 110 and one or more data analytics components 112 that are connected to each other as shown in FIG. 2. In this implementation of the backend component, the one or more front end components 108 may perform various actions with respect to the incoming key action data from each user. For example, the one or more front end components 108 may unpack the key action data stream, rename the key action data stream, move the key action data stream to a designated folder and update a set of log files about the key action data streams. The one or more front end components 108 may be implemented as one or more desktop computers, one or more laptop computers or one or more cloud computing resources and may execute various pieces of software/code including, for example, Windows, Perl, Java Scripts, Microsoft Office and Visual basic. The one or more data stores 110 may be used to store the various key action data streams and may segregate the key action data stream for each user into a separate storage area, such as a folder for example. The one or more data stores 110 may be implemented in a general purpose computer, specialized computer for high volume storage and complex access or a combination of hardware and software and may execute various pieces of software/code including, for example, Excel and Windows Explorer. The one or more data analytics components 112 may process each key action data file in order to convert that file into a common profile format and then update any statistics and profile about the user as described below in more detail. The one or more data analytics components 112 may be implemented using a general purpose computer and may execute various pieces of software/code including, for example, Excel, other statistical packages, such as SPSS, R and big data analytics.

Figure 4:
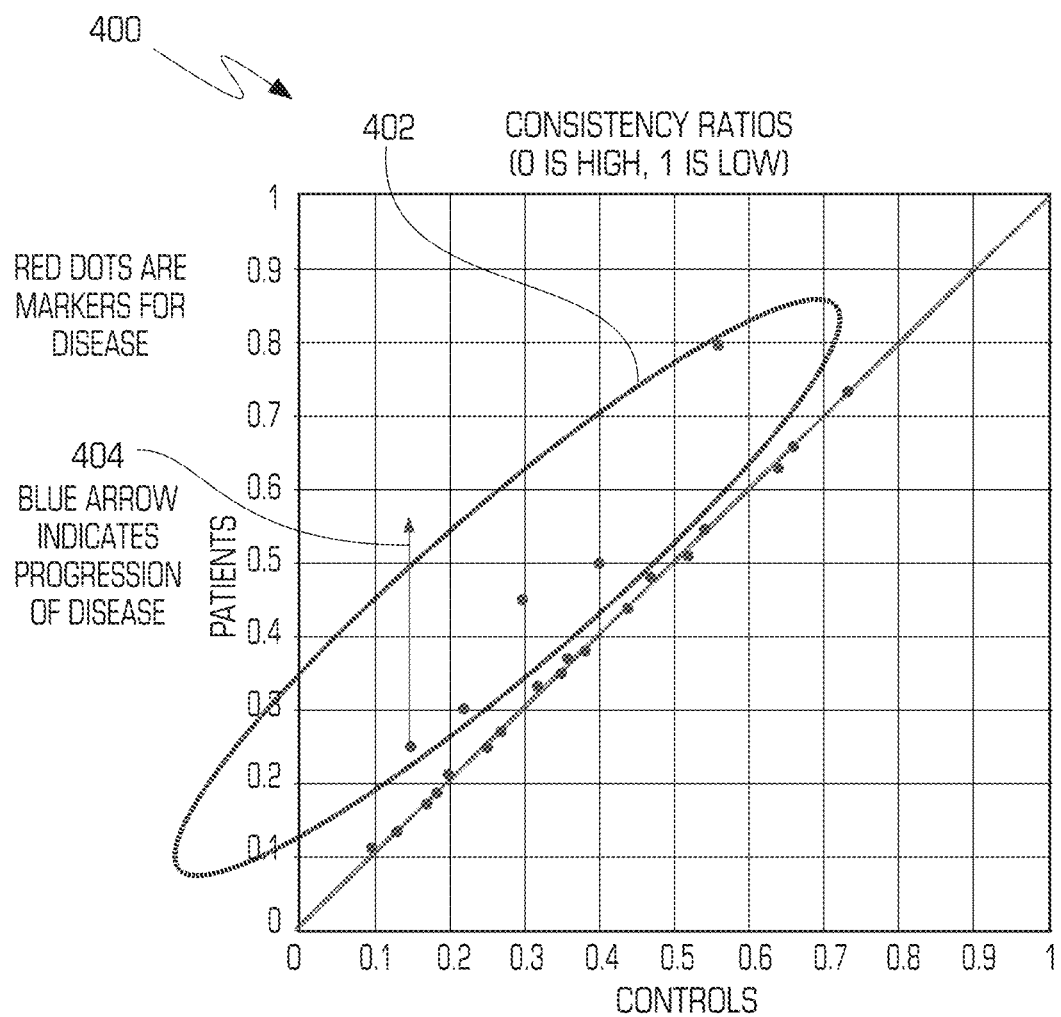
FIG. 4 illustrates an example of the data generated by the system shown in FIG. 1.

FIG. 4 illustrates an example of the data generated 400 by the system shown in FIG. 1. In particular, the graph 400 shows the consistency ratios for a set of control subjects (that do not have any neurological disorder) and a set of patients with some neurological disorder. The consistency ratios may range from 0 (high consistency ratio) to 1 (low consistency ratio.) As shown in the graph, the control subjects have data values for a key action cadence that are near the midline indicating normal cognitive function. In contrast, the patients have data points 402 above the midline that are markers for a neurological condition. In the graph in FIG. 4, the key action data (described elsewhere) may be used to calculate the inconsistency values shown in FIG. 4. For example, a coefficient of variance algorithm may be used as well as other algorithms to determine the inconsistency values. In addition, an arrow 404 superimposed on the graph and its data shows the data values changes that show a progression of the cognitive disease.

Figure 5:
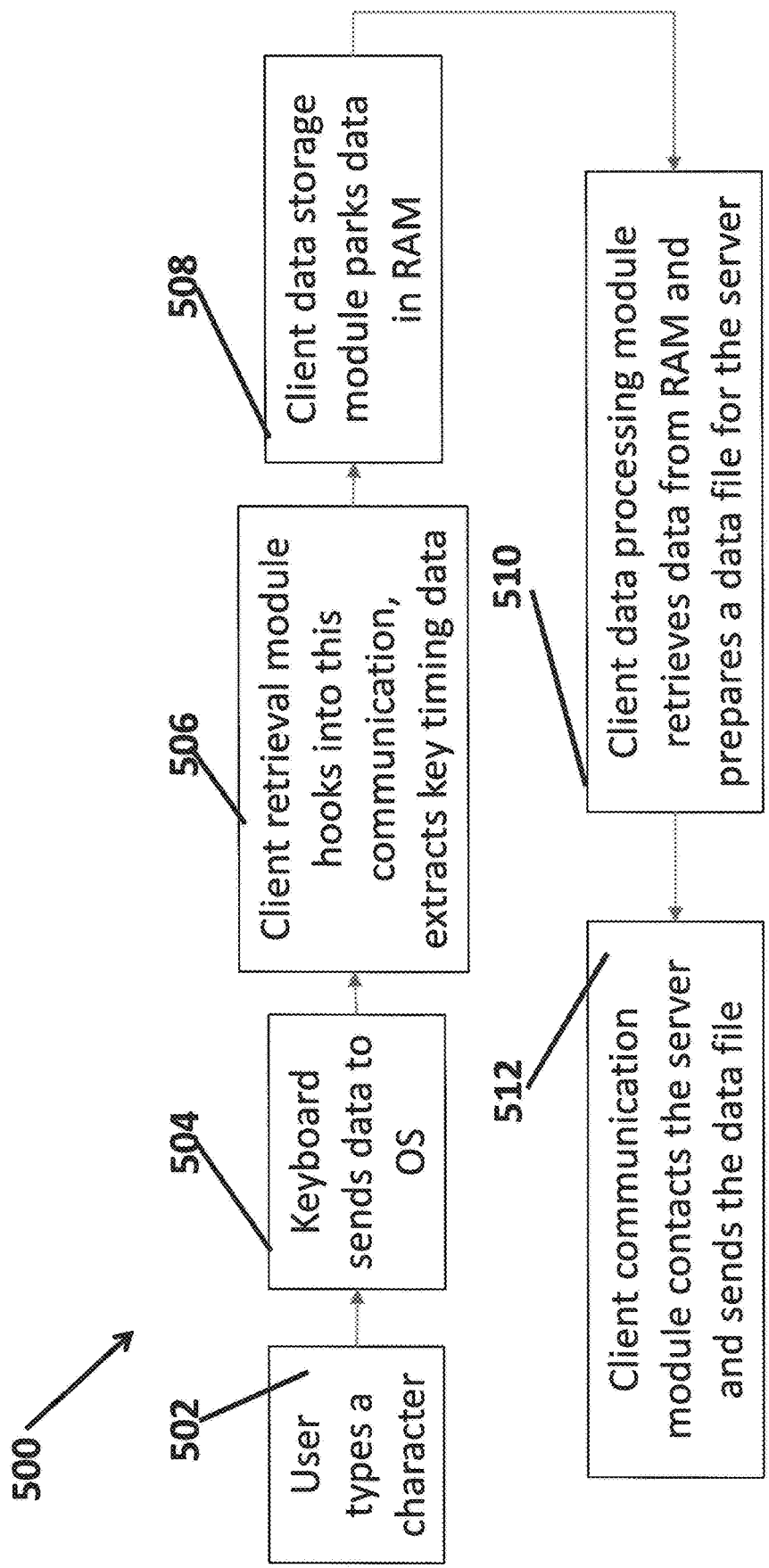
FIG. 5 illustrates an example of the processes performed by each computing device of the system for detecting and monitoring a neurological 5 disorder.

FIG. 5 illustrates an example of the processes 500 performed by each computing device of the system for detecting and monitoring a neurological disorder. When the user types a character on the input device (502), the input device records data related to each key event/action. The key events/actions may be either a key press action (key-down) or a release of a key (keyup.) For each such event/action, the input device records the key identifier, the action being performed on the identified key and the clock time in long times, i.e. the time in milliseconds since Jan. 1, 1950. Once the key event/action data has been recorded, the key event data may be sent to the OS (operating system) (504). The typing cadence component may hook into this communication and extracts the data being sent (506) using a standard known API. The data that is extracted by the typing cadence component may be stored (508) in the computing device. In one embodiment, the data may be stored in the memory of the computing device. When the key action data stored in the computing device reaches a certain threshold (which can be set by a customer and changed remotely) or other events (such as computer shut down), the typing cadence component may trigger the sending of a data file and the typing cadence component may prepare the data file to be sent to the server (510). During the preparation of the key action data file, the typing cadence component may calculate differential times, i.e. the time a key is held down and then released (aka dwell time) and the time between key-down on one key and keydown on the next key (aka flight time) based on the extracted key action data. The key action data (and the calculated differential times) then may be sent to the backend component (512.) In some embodiments, the key action data file from each computing device may be encrypted for security so that the backend component may perform decryption on the key action data files. In one embodiment, the key action data file may have a format that may include:

(1) Key 1 identification
(2) Key 2 identification (if the same as Key 1, dwell time; if different, flight time; and
(3) Time1, time2, time3, time4, etc. data points for every time a Key1-Key2 sequence occurred.

An example of the key action data file having this format is shown in more detail in Appendix A that was discussed above in more detail.

Figure 6:
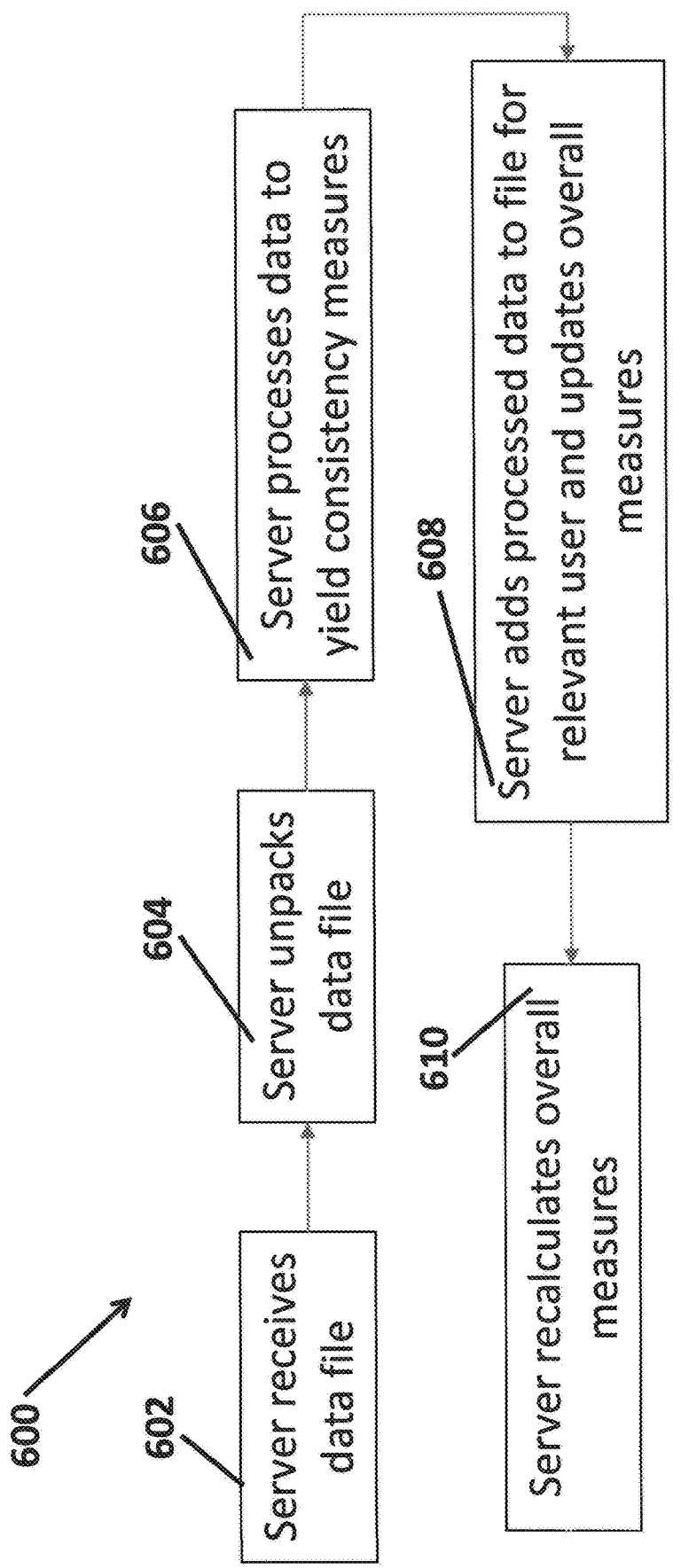
FIG. 6 illustrates an example of the processes performed by the backend component of the system for detecting and monitoring a neurological disorder.

FIG. 6 illustrates an example of the processes 600 performed by the backend component of the system for detecting and monitoring a neurological disorder. The backend component 106 may receive the key action data file (602) and may then unpack the data file, which may be in a .bin format and converts into a .csv format (spreadsheet format)

to be read in Excel or other protocols (604). The backend component may process and use the key action cadence data to calculate various statistical properties, including a measure of consistency (606).

The backend component may then add the processed data to a file for the relevant user and update overall measures (608). The overall measures may be, for example, weighted averages determined based on the measure of inconsistency values. The backend component may then recalculate the overall measures (610) which are used to detect and then monitor a neurological disorder as shown in FIG. 4.

Further details of the above typing cadence system and method are described in U.S. patent application Ser. No. 14/318,477, filed on Jun. 27, 2014 and entitled "Neurological Disorder Determining And Monitoring System And Method", the entirety of which is incorporated by reference herein.

The above system may be part of the system and method for continuous monitoring for CNS diseases. The system for continuous monitoring addresses the need for early and precise diagnosis of CNS diseases. The system uses a method for recording data, processing data locally, sending data to the server and the server's additional processing of data. The system and method addresses the need to provide CNS treating doctors and their patients with accurate, precise and ongoing measurement of cognitive function. Preferably, patients and doctors would be able to see data representing small time increments. The method for recording, preprocessing, sending to server and processing at server is the same as for the above mentioned system implementation described above with reference to FIGS. 1-6. However, the frequency of collecting and processing data, as well as display of data is different.

Figure 7:
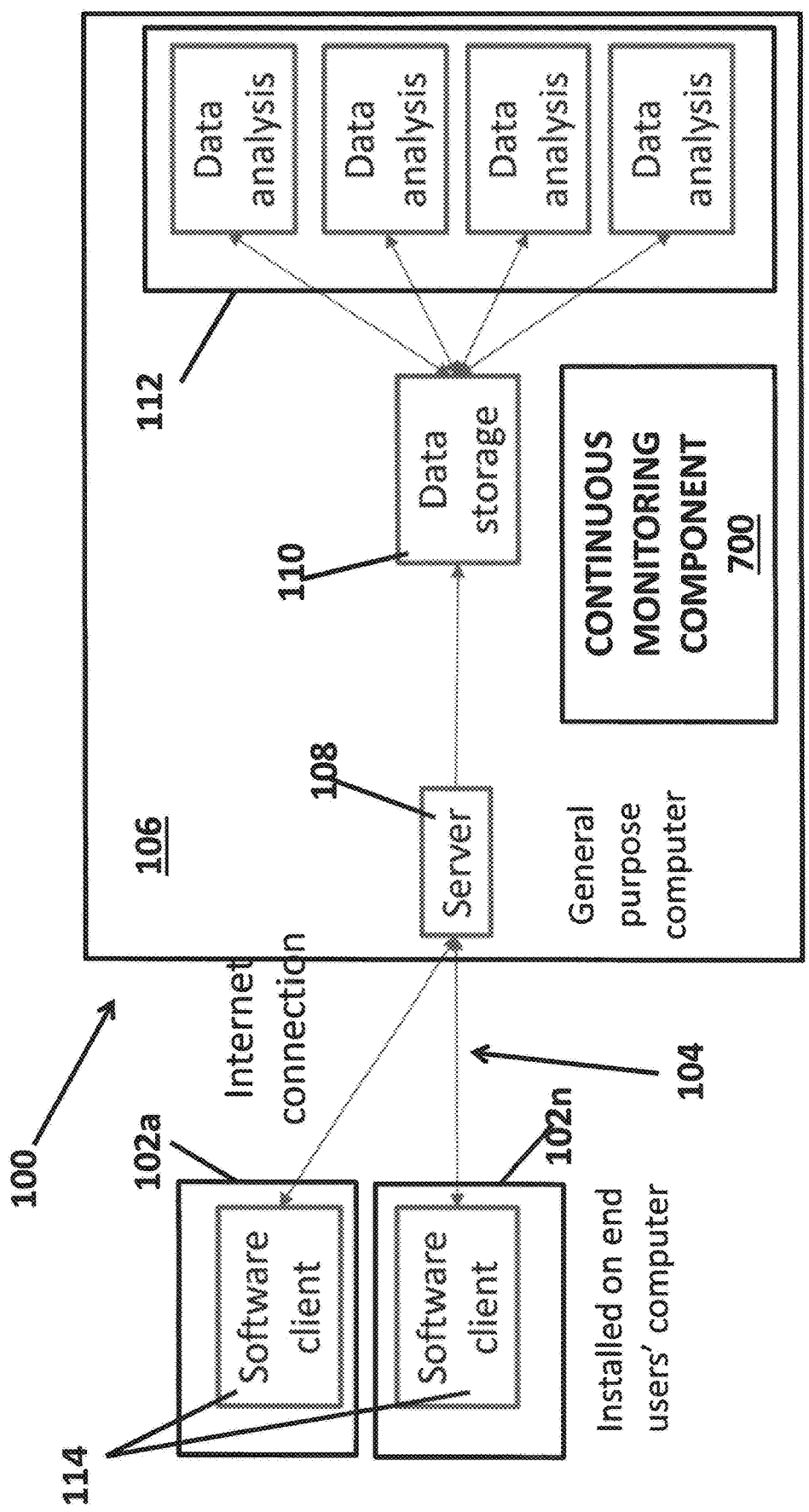
FIG. 7 illustrates a system for detecting and monitoring a neurological disorder with a first embodiment of a continuous monitoring component.

FIG. 7 illustrates a system 100 for detecting and monitoring a neurological disorder with a first embodiment of a continuous monitoring component 700 that is integrated into the system 100. In this embodiment, the continuous monitoring component 700 may receive typing cadence data that is being sent to the server 108 as described above. The continuous monitoring component 700 may be implemented in hardware or software. When the continuous monitoring component is implemented in hardware, it may be an ASIC, programmable logic device, an integrated circuit, a state machine or a microcontroller that operate to perform the functions and operations of the continuous monitoring component as described below. When the continuous monitoring component is implemented in software, it may be a plurality of lines of code that may be stored on a computer, such as the backend system 106 in FIG. 1 or any other computer system and then executed by a processor of the computer so that the processor is configured to perform the functions and operations of the continuous monitoring component described below.

Figure 8:
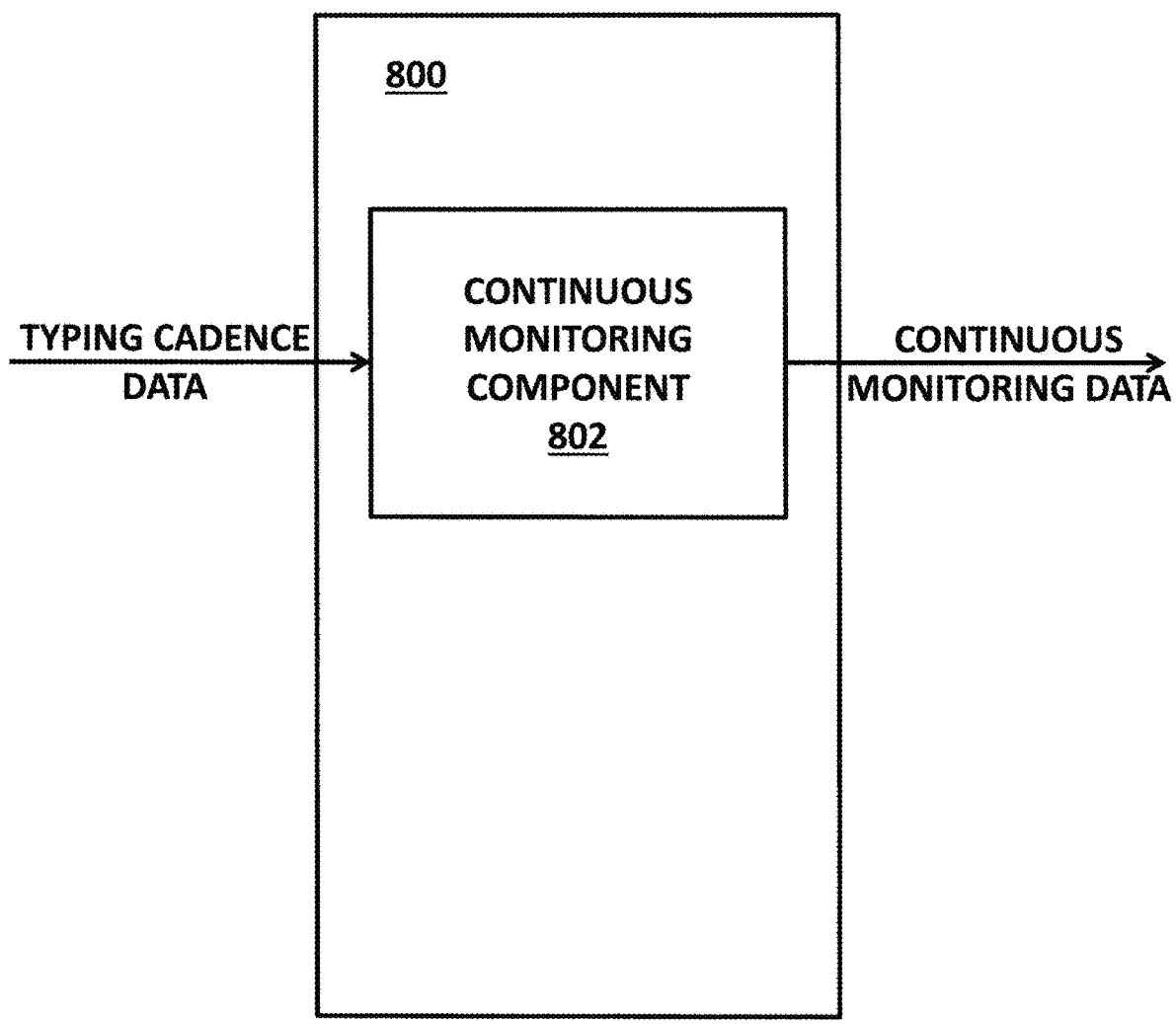
FIG. 8 illustrates a second embodiment of the continuous monitoring system that is a standalone system.

FIG. 8 illustrates a second embodiment of the continuous monitoring system that is a standalone system 800 in which the continuous monitoring component 802 is part of that system 800 that may be a computer system with the usual components. In this embodiment, the continuous monitoring component 802 may receive typing cadence data from an outside source. The continuous monitoring component 802 may be implemented in hardware or software. When the continuous monitoring component is implemented in hardware, it may be an ASIC, programmable logic device, an integrated circuit, a state machine or a microcontroller that operate to perform the functions and operations of the continuous monitoring component as described below. When the continuous monitoring component is implemented in software, it may be a plurality of lines of code that may be stored on a computer, such as the backend system 106 in FIG. 1 or any other computer system and then executed by a processor of the computer so that the processor is configured to perform the functions and operations of the continuous monitoring component described below.

In each of the embodiments shown in FIGS. 7 and 8, typing cadence data may arrive at the continuous monitoring component so that the data may be processed and displayed (described in more detail below with reference to FIG. 10). In each of the embodiments shown in FIGS. 7 and 8, the typing cadence data may be periodically received by the continuous monitoring component, such as many times a day or even several times an hour and then displayed as continuous monitoring typing cadence data. The typing cadence data may be gathered, processed and sent to the continuous monitoring component 700, 802 in small increments. The size of the increments is adjustable depending on the application. For example, for building a baseline data set, the system and method may set the increment value at 20000 while, for continuous monitoring, the system and method may set the increment value to 1000 or less.

Figure 11:
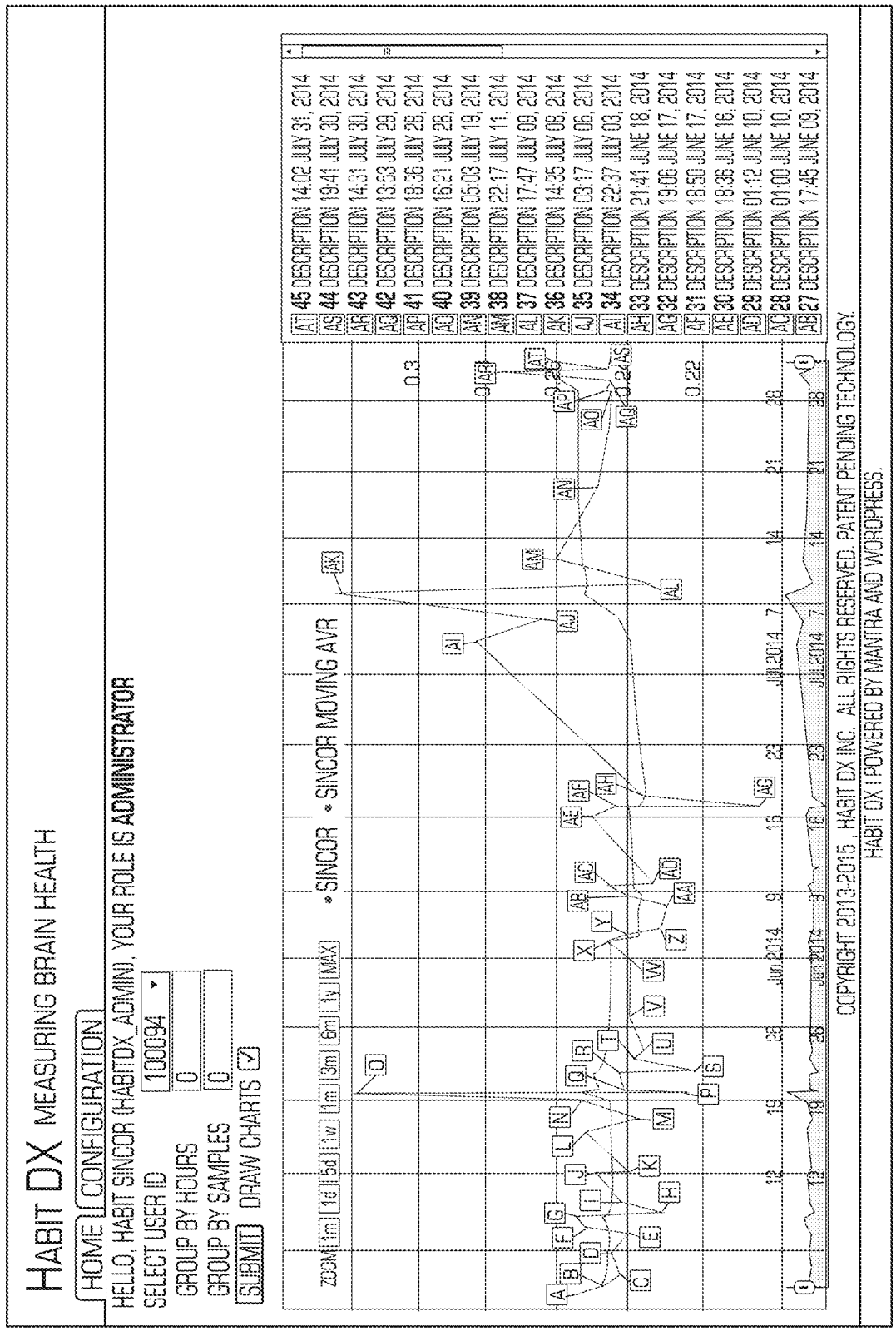
FIG. 11 shows an example of a chart generated by the system.

The continuous monitoring component 700, 802 may process the data in the same small increments and add a data point indication, such as a point on a graph or chart for a particular patient whose typing cadence data is being received, so that the doctor, patient or patients could view the continuous monitoring output data. FIG. 11 shows an example of a chart generated by the system. In some embodiments, each of the doctor, patient or patients may view the continuous monitoring output data on the computing devices 102 shown in FIG. 7 for example. The embodiment shown in FIG. 8 may also have the capability to allow each doctor, patient or patients to access the system 800 using a computing device 102 (not shown) and then display the continuous monitoring output data.

Figure 9:
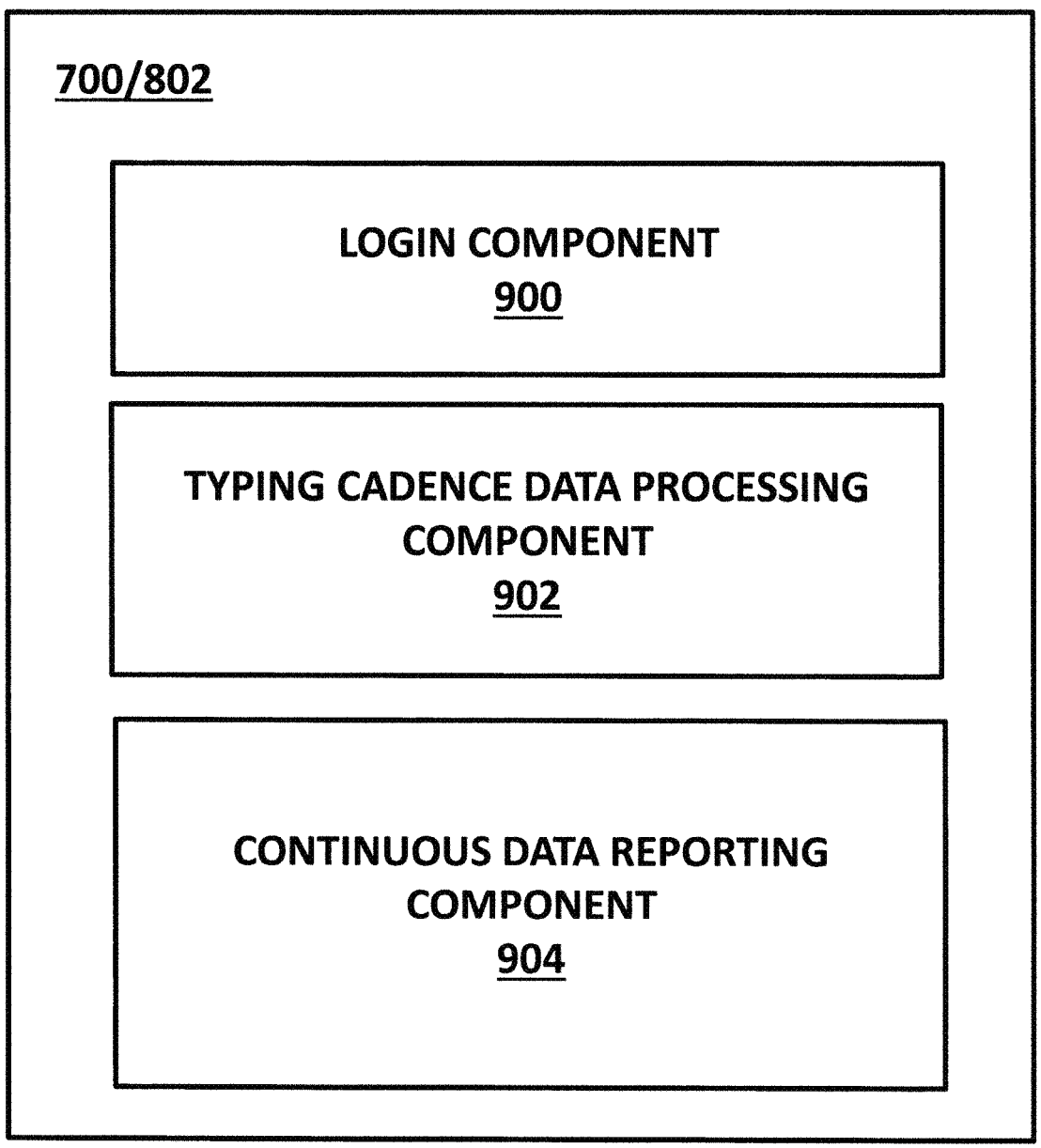
FIG. 9 illustrates further details of the continuous monitoring component shown in FIGS. 7 and 8.

In some embodiments, the system 100, 800 may include a web site (that may be generated and populated in some embodiment, by the continuous data reporting component 904 shown in FIG. 9) that enables users, doctors and patients to view the continuous monitoring output data when the users, doctors and patients are properly authenticated by the system in a known manner. In the case of a doctor accessing the continuous monitoring output data, the doctor may choose which patient's data to view. For a patient with the appropriate authenticated access, the patient can only view their own data. When any user is accessing the continuous monitoring output data, the user may select which time period of data to view and select the form of the display, such as charts, tables or other forms. After all the fields are completed by the user and the request is sent to the system 100, 800, the continuous monitoring component 700, 802 aggregates the relevant data (based on the user request) and displays the data, such as on the web page for the user using, for example, a browser application on each computing device 102.

FIG. 9 illustrates further details of the continuous monitoring component 700, 802 in FIGS. 7 and 8. Specifically, the continuous monitoring component 700, 802 may have a login component 900, a typing cadence data processing component 902 and a continuous data reporting component 904. Each of these components may be implemented in software or hardware as described above.

The login component 900 may permit a doctor to register for the continuous monitoring and invite/register all the patients they wish to be measured using the continuous monitoring system. The doctors and patients may use the secure login that the system employs. The login component 900 may implement an authentication method to ensure that both the doctor and the patient are who they are supposed to be.

The data processing component 902 may perform the typing cadence data processing as described below with reference to FIG. 10. The continuous data reporting component 904 may prepare and generate the continuous data reports that may be sent to the authorized users of the system. The continuous data reports may have various forms and may be delivered to the users as a web page on a web site or as a file having a particular data format.

In another implementation, the user, whether a doctor or patient, may choose continuous data reporting for the system. In the continuous data reporting mode, any time another data point was received for the patient (in the case of a patient user) or a patient being treated by the doctor (for a doctor user) at the continuous monitoring component 700, 802, the data reporting, such as a chart, table, web page, etc., would be updated with this most recent data and provided to the user. In another implementation, the data shown to each user by the continuous data reporting component 904 may include not only the raw data, but also a moving average, to highlight for the user where the true extremes are in the captured data.

Figure 10:
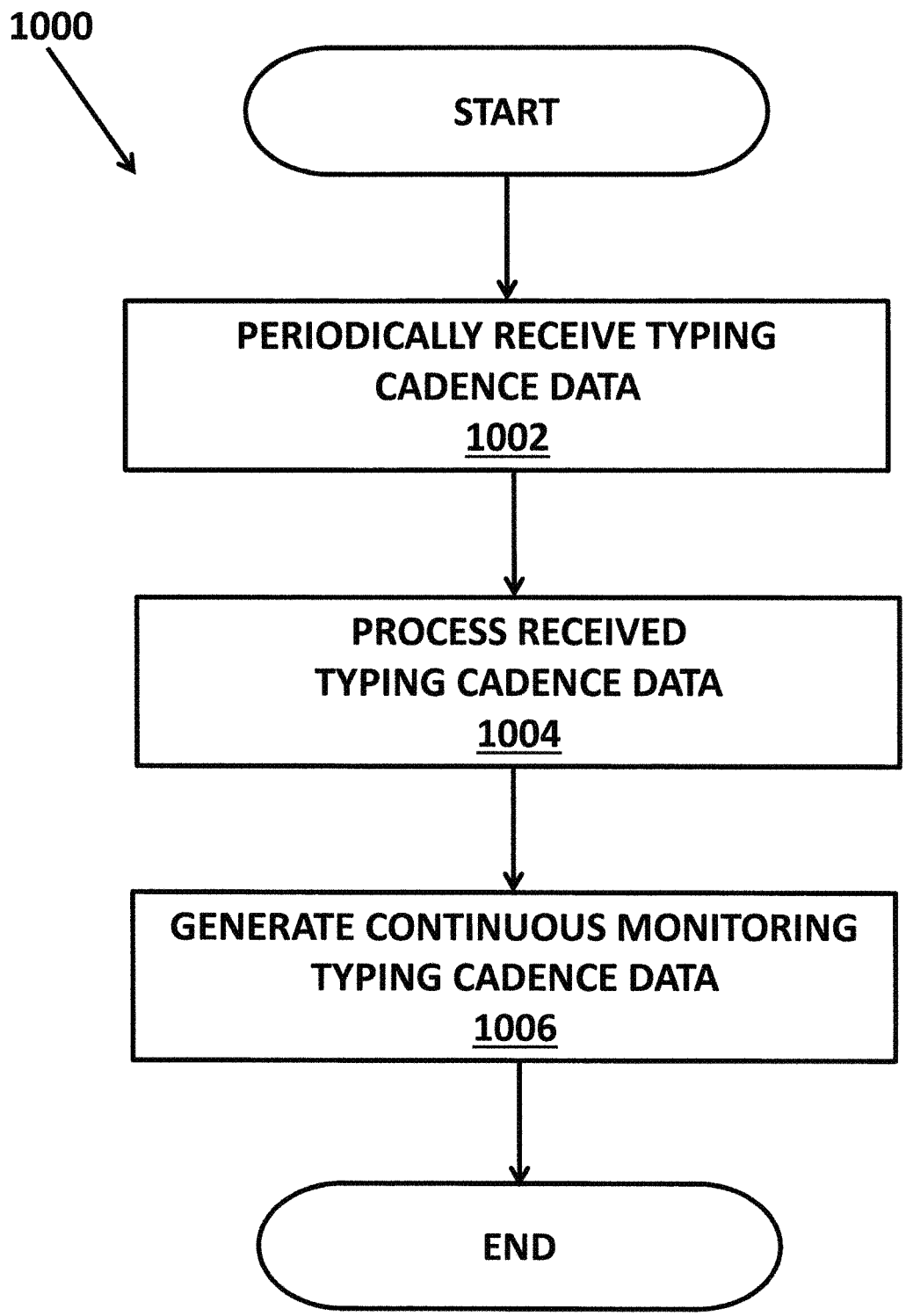
FIG. 10 illustrates a continuous monitoring method that may use the continuous monitoring component.

FIG. 10 illustrates a continuous monitoring method 1000 that may use the continuous monitoring component to implement the method or the method may be implemented using other elements and components since the method is not limited to operating on/with the continuous monitoring component described above. In the method, typing cadence data may be periodically received (1002). The periodicity of the received data may be varied, but may be, for example, several times an hour for a particular patient or a particular doctor that may have one or more patients. The received typing cadence data may be processed (1004). For example, the data may be unpacked from the received data file for each computing device, may determine to which user the particular computing device relates based on the file header of the particular data file, may convert the data from the format it was sent in into a common format, may calculate the profile data for the particular patient and may place the data and profile in the right folder in the data storage. The processed typing cadence data may then be used to generate a continuous monitoring typing cadence output data (1006) that may be, for example, the chart shown in FIG. 4. The continuous monitoring typing cadence output data may also be the raw typing cadence data, a table of the typing cadence data or the exemplary graph shown in FIG. 11. The method may repeat the processes 1002-1006 as each new piece/batch of typing cadence data is received.

FIG. 11 shows an example of a chart in a user interface of the system described above that is generated by the system based on the patient data. In the chart, data about the patient is plotted for the patient at different times as shown on the horizontal axis of the chart. The vertical axis of the chart are the values for each time data point of the patient.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

The system and method described above improve another technology or technical field in that the system and method improves medical diagnosis technology for central nervous system diseases using typing cadence. The system and method improve the technical field of medical diagnosis for central nervous system diseases by providing a continuous monitoring apparatus that receives the typing cadence data and generates a data report based on the received cadence data to provide continuous monitoring of a central nervous system disease of the patient.

The system and method may be implemented using a sensor/input device and a computer system, but the computer system is not performing generic computer functions. Specifically, the computer receives typing cadence data and generates a data report based on the received cadence data to provide continuous monitoring of a central nervous system disease of the patient which are not generic computer functions.

The system and method also cause the transformation of an article to a different state. Specifically, the system receives typing cadence data and provides continuous monitoring based on the typing cadence data. Thus, an article (the typing cadence data) is transformed into continuous monitoring of the central nervous system disease of the patient.

While the foregoing has been with reference to a particular embodiment of the disclosure, it will be appreciated by those skilled in the art that changes in this embodiment may be made without departing from the principles and spirit of the disclosure, the scope of which is defined by the appended claims.

APPENDIX A

Entries 395
Serial 1234

| First Key Press | Second Key Press | TS1 | TS2 | TS3 | TS4 | TS5 | TS6 | TS7 | TS8 | TS9 | TS10 |
|---:|---:|---:|---:|---:|---:|---:|---:|---:|---:|---:|---:|
| 8 | 8 | 104 | 80 | 104 | 104 | 120 | 176 | 120 | 104 | 144 | 72 |
| 32 | 8 | 5632 | 10079 | | | | | | | | |
| 69 | 8 | 1560 | | | | | | | | | |
| 79 | 8 | 3368 | 9471 | | | | | | | | |
| 83 | 8 | 5232 | 3279 | | | | | | | | |
| 84 | 8 | 1288 | | | | | | | | | |
| 87 | 8 | 2320 | | | | | | | | | |
| 89 | 8 | 2296 | | | | | | | | | |
| 187 | 8 | 1448 | | | | | | | | | |
| 13 | 13 | 112 | 88 | 80 | 128 | 88 | 120 | 97 | 112 | 96 | 144 |
| 32 | 13 | 5943 | | | | | | | | | |
| 78 | 13 | 4408 | | | | | | | | | |
| 83 | 13 | 3416 | | | | | | | | | |
| 190 | 13 | 1960 | 936 | 1280 | 22431 | 4415 | 17024 | | | | |
| 191 | 13 | 15288 | | | | | | | | | |
| 32 | 32 | 96 | 96 | 88 | 80 | 96 | 96 | 96 | 88 | 71 | 72 |
| 54 | 32 | 1280 | | | | | | | | | |
| 65 | 32 | 2327 | 168 | 160 | 160 | 232 | 145 | 192 | | | |
| 66 | 32 | 216 | | | | | | | | | |
| 67 | 32 | 2568 | 6007 | | | | | | | | |
| 68 | 32 | 488 | 240 | 3176 | 144 | 144 | 3008 | 88 | 3645 | 1232 | 112 |
| 69 | 32 | 160 | 328 | 240 | 224 | 216 | 1400 | 1528 | 712 | 152 | 176 |
| 70 | 32 | 936 | 168 | 160 | 160 | 176 | 144 | 1312 | 152 | 216 | 136 |
| 71 | 32 | 416 | 240 | 257 | 936 | 3328 | 368 | 1536 | 2328 | 10943 | 296 |
| 72 | 32 | 256 | 224 | 264 | 296 | 1104 | 1488 | | | | |
| 75 | 32 | 1776 | 2335 | 1552 | | | | | | | |
| 76 | 32 | 2431 | 3424 | 1128 | 400 | 2488 | 488 | 1160 | 1303 | | |
| 77 | 32 | 280 | 1344 | 2616 | | | | | | | |
| 78 | 32 | 192 | 192 | 1767 | 215 | 216 | 496 | 248 | 216 | 296 | 416 |
| 79 | 32 | 272 | 321 | 320 | 264 | 312 | 288 | 928 | 5192 | 288 | 256 |
| 80 | 32 | 4816 | 496 | | | | | | | | |
| 82 | 32 | 1096 | 135 | 120 | 304 | 424 | 208 | 4943 | 184 | 126 | 232 |
| 83 | 32 | 312 | 192 | 2544 | 2440 | 1320 | 3976 | 2160 | 192 | 2344 | 1600 |
| 84 | 32 | 360 | 296 | 1296 | 464 | 416 | 280 | 296 | 280 | 304 | 264 |
| 85 | 32 | 248 | | | | | | | | | |
| 87 | 32 | 1640 | 192 | 2376 | 7895 | 400 | | | | | |
| 89 | 32 | 4264 | 856 | 720 | 2791 | 2343 | 256 | 280 | 280 | 1632 | 352 |
| 186 | 32 | 608 | 480 | | | | | | | | |
| 188 | 32 | 256 | 272 | 256 | 192 | 264 | 240 | 208 | 208 | 256 | 240 |
| 189 | 32 | 976 | 976 | | | | | | | | |
| 190 | 32 | 1440 | 256 | 256 | 264 | 1472 | 240 | 408 | 568 | 264 | 272 |
| 37 | 37 | 104 | 80 | 96 | 128 | 104 | 136 | | | | |
| 77 | 37 | 1856 | | | | | | | | | |
| 48 | 48 | 96 | 120 | | | | | | | | |
| 57 | 48 | 1160 | | | | | | | | | |
| 186 | 48 | 328 | | | | | | | | | |
| 32 | 49 | 2799 | | | | | | | | | |
| 49 | 49 | 191 | 129 | 120 | | | | | | | |
| 186 | 49 | 1695 | | | | | | | | | |
| 32 | 50 | 592 | 824 | | | | | | | | |
| 48 | 50 | 424 | | | | | | | | | |
| 50 | 50 | 88 | 120 | 96 | | | | | | | |
| 49 | 54 | 273 | | | | | | | | | |
| 50 | 54 | 320 | | | | | | | | | |
| 54 | 54 | 96 | 96 | | | | | | | | |
| 49 | 57 | 592 | | | | | | | | | |
| 57 | 57 | 73 | 119 | | | | | | | | |
| 32 | 65 | 7615 | 200 | 584 | 840 | 216 | 832 | 896 | 208 | 208 | 2135 |
| 65 | 65 | 88 | 128 | 119 | 120 | 184 | 136 | 168 | 96 | 136 | 168 |
| 66 | 65 | 216 | | | | | | | | | |
| 67 | 65 | 216 | 216 | 512 | 392 | 608 | 416 | 464 | 431 | | |
| 68 | 65 | 408 | 344 | | | | | | | | |
| 69 | 65 | 216 | 288 | 368 | 328 | 616 | 296 | 352 | 424 | 344 | 336 |
| 70 | 65 | 232 | 288 | | | | | | | | |
| 71 | 65 | 368 | 359 | | | | | | | | |
| 72 | 65 | 424 | 288 | 480 | 304 | 584 | 424 | 240 | 168 | 400 | 368 |
| 73 | 65 | 488 | | | | | | | | | |
| 75 | 65 | 256 | | | | | | | | | |
| 76 | 65 | 160 | 601 | 631 | 288 | 513 | | | | | |
| 77 | 65 | 368 | 423 | 216 | 976 | 352 | 256 | 464 | 336 | 392 | |
| 78 | 65 | 464 | 464 | | | | | | | | |
| 79 | 65 | 936 | | | | | | | | | |
| 80 | 65 | 632 | 464 | 432 | | | | | | | |
| 82 | 65 | 216 | 856 | 560 | 600 | 344 | 360 | 792 | | | |
| 84 | 65 | 248 | 296 | 288 | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 86 | 65 | 424 | 416 | 416 | 400 | 568 | | | | | |
| 87 | 65 | 280 | 320 | 432 | 360 | 256 | | | | | |
| 32 | 66 | 976 | 264 | 215 | 312 | 256 | 1112 | 264 | 208 | 1184 | 264 |
| 65 | 66 | 160 | 192 | | | | | | | | |
| 66 | 66 | 120 | 80 | 72 | 80 | 96 | 72 | 64 | 96 | 88 | 96 |
| 69 | 66 | 704 | | | | | | | | | |
| 73 | 66 | 280 | | | | | | | | | |
| 79 | 66 | 352 | | | | | | | | | |
| 85 | 66 | 288 | | | | | | | | | |
| 160 | 66 | 192 | 168 | 159 | | | | | | | |
| 32 | 67 | 240 | 1568 | 240 | 288 | 351 | 424 | 472 | 4816 | 840 | 496 |
| 65 | 67 | 216 | 192 | 448 | | | | | | | |
| 67 | 67 | 72 | 120 | 144 | 144 | 96 | 96 | 72 | 104 | 137 | 160 |
| 69 | 67 | 304 | 304 | 328 | | | | | | | |
| 73 | 67 | 216 | 392 | 265 | 327 | 352 | | | | | |
| 78 | 67 | 248 | 232 | 216 | 216 | 232 | | | | | |
| 82 | 67 | 304 | 216 | | | | | | | | |
| 83 | 67 | 2304 | 352 | 272 | 288 | 280 | 312 | | | | |
| 85 | 67 | 288 | 304 | 256 | 256 | 256 | | | | | |
| 160 | 67 | 352 | 208 | | | | | | | | |
| 189 | 67 | 376 | | | | | | | | | |
| 32 | 68 | 1191 | 1344 | 376 | 68029 | 1096 | | | | | |
| 65 | 68 | 136 | 344 | | | | | | | | |
| 68 | 68 | 120 | 96 | 104 | 88 | 120 | 112 | 120 | 120 | 88 | 96 |
| 69 | 68 | 336 | 256 | 322 | 328 | 272 | 312 | 320 | 280 | | |
| 73 | 68 | 384 | 256 | 240 | 256 | 168 | | | | | |
| 76 | 68 | 200 | 424 | | | | | | | | |
| 78 | 68 | 360 | 232 | 272 | 256 | 232 | 264 | 256 | 280 | 280 | 280 |
| 79 | 68 | 304 | 392 | 336 | 304 | 352 | | | | | |
| 82 | 68 | 232 | 240 | 288 | | | | | | | |
| 32 | 69 | 232 | 1888 | 496 | 281 | 864 | 216 | 368 | 488 | 232 | 424 |
| 66 | 69 | 240 | 232 | 264 | 359 | 232 | 328 | 280 | 240 | 232 | |
| 67 | 69 | 304 | 368 | 272 | 448 | 304 | 352 | 407 | 456 | 312 | |
| 68 | 69 | 240 | 240 | 256 | 216 | 200 | 192 | 232 | 240 | 231 | 216 |
| 69 | 69 | 96 | 160 | 96 | 104 | 80 | 120 | 144 | 144 | 168 | 80 |
| 70 | 69 | 392 | 520 | | | | | | | | |
| 71 | 69 | 280 | 312 | 368 | 752 | | | | | | |
| 72 | 69 | 304 | 312 | 320 | 384 | 392 | 856 | 384 | 272 | 208 | 424 |
| 73 | 69 | 496 | 279 | 2240 | 232 | 184 | 408 | 288 | 248 | 246 | 264 |
| 75 | 69 | 344 | 216 | 400 | 192 | 240 | 216 | 288 | | | |
| 76 | 69 | 344 | 656 | 256 | 344 | 904 | 232 | | | | |
| 77 | 69 | 440 | 256 | 264 | 256 | 240 | 184 | 848 | 216 | 368 | 1520 |
| 78 | 69 | 256 | 560 | 416 | 160 | 336 | 416 | 424 | 336 | 344 | 328 |
| 80 | 69 | 248 | 216 | 208 | 280 | 432 | | | | | |
| 82 | 69 | 239 | 224 | 240 | 256 | 224 | 312 | 216 | 232 | 215 | 191 |
| 83 | 69 | 208 | 240 | 280 | 256 | 232 | 264 | 264 | 289 | 256 | 240 |
| 84 | 69 | 192 | 384 | 280 | 328 | 264 | 232 | 264 | | | |
| 86 | 69 | 160 | 280 | 200 | 208 | 240 | 184 | 232 | 376 | 288 | 272 |
| 87 | 69 | 200 | 352 | 264 | 232 | 241 | 399 | | | | |
| 89 | 69 | 368 | 240 | 288 | 376 | 345 | | | | | |
| 160 | 69 | 232 | 216 | | | | | | | | |
| 32 | 70 | 384 | 1760 | 233 | 2064 | 400 | 1456 | 360 | 1816 | 232 | 352 |
| 65 | 70 | 240 | | | | | | | | | |
| 68 | 70 | 288 | | | | | | | | | |
| 69 | 70 | 432 | 1680 | | | | | | | | |
| 70 | 70 | 96 | 64 | 136 | 112 | 88 | 96 | 88 | 95 | 112 | 96 |
| 73 | 70 | 344 | 272 | | | | | | | | |
| 79 | 70 | 336 | 304 | 424 | 304 | 288 | 256 | 328 | 328 | 376 | 368 |
| 160 | 70 | 256 | 216 | | | | | | | | |
| 32 | 71 | 312 | 592 | 305 | 328 | 351 | | | | | |
| 65 | 71 | 192 | 192 | | | | | | | | |
| 71 | 71 | 88 | 88 | 88 | 72 | 96 | 96 | 96 | 80 | 88 | 112 |
| 73 | 71 | 400 | 304 | 360 | 312 | 376 | | | | | |
| 78 | 71 | 280 | 336 | 264 | 272 | 304 | 312 | 255 | 360 | 384 | 312 |
| 79 | 71 | 384 | | | | | | | | | |
| 32 | 72 | 304 | 1016 | 976 | 5680 | 328 | 360 | 680 | 1472 | 304 | 280 |
| 67 | 72 | 192 | 192 | 312 | 344 | 448 | 551 | 256 | 232 | 208 | 168 |
| 71 | 72 | 240 | | | | | | | | | |
| 72 | 72 | 96 | 104 | 88 | 96 | 112 | 64 | 96 | 120 | 72 | 80 |
| 83 | 72 | 168 | 192 | 216 | | | | | | | |
| 84 | 72 | 264 | 248 | 288 | 216 | 160 | 184 | 200 | 304 | 192 | 272 |
| 87 | 72 | 256 | 607 | 384 | 200 | | | | | | |
| 8 | 73 | 2815 | 408 | | | | | | | | |
| 32 | 73 | 464 | 312 | 304 | 1112 | 504 | 296 | 376 | 360 | 3136 | 312 |
| 65 | 73 | 312 | | | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 66 | 73 | 744 | 296 | | | | | | | | |
| 67 | 73 | 264 | 264 | 208 | 224 | 280 | | | | | |
| 68 | 73 | 303 | 392 | 264 | 280 | 240 | | | | | |
| 69 | 73 | 264 | 208 | 344 | | | | | | | |
| 70 | 73 | 400 | 176 | 248 | 256 | 320 | | | | | |
| 71 | 73 | 472 | 552 | 4792 | | | | | | | |
| 72 | 73 | 544 | 432 | 488 | 608 | | | | | | |
| 73 | 73 | 88 | 88 | 72 | 72 | 80 | 72 | 88 | 96 | 88 | 64 |
| 75 | 73 | 232 | 304 | 248 | | | | | | | |
| 76 | 73 | 312 | 296 | 240 | 328 | 312 | 296 | 584 | | | |
| 78 | 73 | 296 | 368 | 519 | | | | | | | |
| 79 | 73 | 216 | | | | | | | | | |
| 80 | 73 | 288 | 247 | 311 | | | | | | | |
| 82 | 73 | 216 | 432 | 240 | 728 | 376 | 240 | 240 | 256 | 200 | 304 |
| 83 | 73 | 408 | 312 | 497 | 304 | 217 | 305 | 216 | 344 | | |
| 84 | 73 | 528 | 560 | 544 | 552 | 496 | 264 | 536 | 312 | 136 | 632 |
| 85 | 73 | 536 | 417 | 232 | | | | | | | |
| 86 | 73 | 512 | | | | | | | | | |
| 87 | 73 | 672 | 639 | 288 | 271 | | | | | | |
| 160 | 73 | 544 | 352 | 328 | 256 | 344 | 304 | | | | |
| 74 | 74 | 88 | | | | | | | | | |
| 160 | 74 | 208 | | | | | | | | | |
| 32 | 75 | 1120 | 1992 | | | | | | | | |
| 65 | 75 | 248 | 184 | 384 | 352 | 280 | 240 | | | | |
| 67 | 75 | 264 | 424 | 327 | | | | | | | |
| 69 | 75 | 281 | | | | | | | | | |
| 75 | 75 | 95 | 112 | 80 | 72 | 72 | 104 | 96 | 88 | 96 | 88 |
| 78 | 75 | 472 | | | | | | | | | |
| 82 | 75 | 240 | | | | | | | | | |
| 83 | 75 | 256 | 280 | 230 | 184 | 265 | | | | | |
| 32 | 76 | 320 | 512 | 584 | 752 | 544 | 600 | 2608 | | | |
| 65 | 76 | 536 | 448 | 264 | 303 | 232 | 408 | | | | |
| 66 | 76 | 512 | 616 | 728 | 400 | | | | | | |
| 69 | 76 | 352 | 328 | 344 | 360 | 232 | 625 | 904 | | | |
| 71 | 76 | 648 | | | | | | | | | |
| 73 | 76 | 360 | 304 | 280 | 486 | 344 | 280 | | | | |
| 75 | 76 | 192 | | | | | | | | | |
| 76 | 76 | 96 | 96 | 96 | 96 | 96 | 104 | 72 | 96 | 96 | 104 |
| 78 | 76 | 488 | | | | | | | | | |
| 79 | 76 | 240 | 216 | 256 | 240 | | | | | | |
| 80 | 76 | 224 | 247 | | | | | | | | |
| 82 | 76 | 152 | 600 | 608 | | | | | | | |
| 83 | 76 | 240 | | | | | | | | | |
| 84 | 76 | 680 | | | | | | | | | |
| 85 | 76 | 903 | 560 | 440 | 528 | | | | | | |
| 32 | 77 | 256 | 344 | 2376 | 304 | 1360 | 232 | 560 | 1696 | 984 | 1480 |
| 65 | 77 | 264 | 288 | 216 | 304 | | | | | | |
| 69 | 77 | 952 | 376 | 264 | 464 | | | | | | |
| 73 | 77 | 296 | | | | | | | | | |
| 77 | 77 | 112 | 120 | 136 | 112 | 71 | 96 | 104 | 88 | 48 | 72 |
| 78 | 77 | 1352 | | | | | | | | | |
| 79 | 77 | 400 | 280 | 288 | 312 | 304 | 280 | 328 | | | |
| 80 | 77 | 880 | 496 | | | | | | | | |
| 84 | 77 | 1912 | 464 | 472 | 760 | | | | | | |
| 85 | 77 | 320 | | | | | | | | | |
| 160 | 77 | 608 | 192 | 232 | 376 | | | | | | |
| 8 | 78 | 2592 | | | | | | | | | |
| 32 | 78 | 232 | 248 | 1536 | 256 | 911 | 296 | 904 | 6047 | 1344 | 2440 |
| 65 | 78 | 208 | 280 | 568 | 184 | 264 | 264 | 224 | 296 | 144 | 264 |
| 69 | 78 | 176 | 313 | 352 | 408 | 208 | 256 | 144 | 256 | 184 | 184 |
| 71 | 78 | 280 | | | | | | | | | |
| 72 | 78 | 264 | | | | | | | | | |
| 73 | 78 | 280 | 296 | 328 | 344 | 304 | 288 | 288 | 304 | 248 | 272 |
| 75 | 78 | 5880 | | | | | | | | | |
| 78 | 78 | 96 | 96 | 96 | 72 | 96 | 88 | 96 | 64 | 64 | 48 |
| 79 | 78 | 400 | 296 | 320 | 288 | 304 | 328 | 328 | 328 | 336 | 328 |
| 82 | 78 | 96 | 256 | 304 | | | | | | | |
| 83 | 78 | 152 | | | | | | | | | |
| 85 | 78 | 367 | 249 | 288 | 304 | 240 | 256 | 264 | 280 | 304 | 344 |
| 87 | 78 | 1072 | 240 | | | | | | | | |
| 8 | 79 | 496 | | | | | | | | | |
| 32 | 79 | 552 | 1840 | 408 | 2599 | 680 | 424 | 368 | 752 | 8295 | 352 |
| 67 | 79 | 216 | 512 | 272 | 464 | 256 | 368 | 296 | 280 | 216 | 256 |
| 68 | 79 | 512 | | | | | | | | | |
| 69 | 79 | 4408 | | | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 70 | 79 | 535 | 280 | 264 | 568 | 272 | 264 | 280 | | | |
| 71 | 79 | 624 | 432 | | | | | | | | |
| 72 | 79 | 424 | 656 | 488 | 530 | 496 | 472 | 360 | | | |
| 73 | 79 | 216 | 208 | 232 | 216 | 216 | 200 | 216 | 216 | 231 | 240 |
| 76 | 79 | 264 | 296 | 256 | 328 | 224 | 288 | 216 | | | |
| 77 | 79 | 312 | 536 | 416 | 568 | 336 | 344 | | | | |
| 78 | 79 | 432 | 648 | 376 | 352 | 296 | 328 | 528 | 552 | 760 | 560 |
| 79 | 79 | 96 | 88 | 96 | 72 | 81 | 96 | 88 | 96 | 96 | 128 |
| 80 | 79 | 240 | 240 | 1128 | 240 | 288 | 392 | | | | |
| 82 | 79 | 280 | 424 | 288 | 192 | 240 | 256 | 208 | 256 | 343 | 328 |
| 83 | 79 | 208 | 384 | 336 | 528 | 312 | 280 | 248 | 544 | | |
| 84 | 79 | 304 | 1071 | 440 | 712 | 256 | 536 | 560 | 344 | 208 | 264 |
| 86 | 79 | 400 | 376 | 656 | | | | | | | |
| 87 | 79 | 760 | | | | | | | | | |
| 89 | 79 | 192 | 256 | 240 | | | | | | | |
| 32 | 80 | 872 | 408 | 336 | 512 | 608 | 440 | 728 | 584 | 984 | 945 |
| 50 | 80 | 1384 | | | | | | | | | |
| 54 | 80 | 2175 | | | | | | | | | |
| 65 | 80 | 424 | 312 | | | | | | | | |
| 69 | 80 | 424 | 328 | | | | | | | | |
| 77 | 80 | 312 | 512 | 576 | | | | | | | |
| 78 | 80 | 632 | | | | | | | | | |
| 79 | 80 | 232 | 1096 | 680 | | | | | | | |
| 80 | 80 | 88 | 72 | 104 | 80 | 104 | 72 | 95 | 96 | 120 | 104 |
| 82 | 80 | 216 | 208 | | | | | | | | |
| 83 | 80 | 984 | 256 | 232 | 425 | 304 | | | | | |
| 85 | 80 | 488 | 512 | 576 | | | | | | | |
| 88 | 80 | 216 | | | | | | | | | |
| 89 | 80 | 264 | | | | | | | | | |
| 32 | 81 | 439 | 448 | | | | | | | | |
| 81 | 81 | 104 | 120 | | | | | | | | |
| 32 | 82 | 856 | 152 | 168 | 136 | 208 | 4032 | 176 | 192 | 704 | 216 |
| 65 | 82 | 407 | 192 | 256 | 160 | 240 | 191 | 184 | 200 | 152 | 192 |
| 66 | 82 | 408 | | | | | | | | | |
| 67 | 82 | 337 | | | | | | | | | |
| 68 | 82 | 1264 | | | | | | | | | |
| 69 | 82 | 24 | 240 | 280 | 176 | 112 | 248 | 152 | 264 | 168 | 240 |
| 70 | 82 | 472 | 464 | | | | | | | | |
| 71 | 82 | 280 | 305 | | | | | | | | |
| 73 | 82 | 280 | 200 | | | | | | | | |
| 79 | 82 | 240 | 656 | 249 | 360 | 264 | 672 | 352 | 240 | 329 | 312 |
| 80 | 82 | 416 | 280 | 360 | 328 | 280 | 336 | 352 | | | |
| 82 | 82 | 136 | 144 | 104 | 72 | 120 | 144 | 72 | 120 | 120 | 96 |
| 84 | 82 | 232 | 216 | | | | | | | | |
| 85 | 82 | 304 | 328 | 416 | 280 | 232 | 256 | 391 | 232 | 424 | |
| 189 | 82 | 304 | | | | | | | | | |
| 8 | 83 | 336 | 1184 | | | | | | | | |
| 32 | 83 | 192 | 360 | 232 | 888 | 424 | 256 | 184 | 1120 | 232 | 192 |
| 48 | 83 | 4088 | | | | | | | | | |
| 65 | 83 | 280 | 240 | 384 | 328 | 296 | 280 | 264 | | | |
| 66 | 83 | 288 | | | | | | | | | |
| 69 | 83 | 344 | 256 | 328 | 280 | 240 | 312 | 304 | 288 | 336 | 312 |
| 73 | 83 | 303 | 368 | 456 | 423 | 610 | 304 | 472 | 224 | 312 | 400 |
| 78 | 83 | 560 | 1992 | 424 | 336 | 360 | 1647 | 279 | 264 | | |
| 79 | 83 | 254 | | | | | | | | | |
| 80 | 83 | 520 | | | | | | | | | |
| 82 | 83 | 400 | 352 | 176 | 183 | 192 | 216 | 256 | 1208 | 27558 | |
| 83 | 83 | 96 | 88 | 96 | 96 | 88 | 136 | 112 | 112 | 112 | 135 |
| 84 | 83 | 696 | 208 | 192 | 232 | 280 | 464 | 616 | | | |
| 85 | 83 | 448 | 360 | 232 | 320 | | | | | | |
| 89 | 83 | 256 | | | | | | | | | |
| 160 | 83 | 960 | 544 | | | | | | | | |
| 222 | 83 | 264 | 496 | 392 | | | | | | | |
| 32 | 84 | 1016 | 2160 | 1608 | 368 | 1032 | 376 | 232 | 1520 | 1360 | 2680 |
| 65 | 84 | 280 | 288 | 296 | 216 | 160 | 264 | 224 | 192 | 328 | 240 |
| 67 | 84 | 488 | 320 | | | | | | | | |
| 69 | 84 | 232 | 184 | 144 | 336 | 272 | 160 | 168 | 3696 | | |
| 72 | 84 | 288 | | | | | | | | | |
| 73 | 84 | 368 | 392 | 1624 | 744 | 1880 | 360 | 360 | 303 | 376 | 264 |
| 76 | 84 | 376 | | | | | | | | | |
| 78 | 84 | 352 | 432 | 288 | 384 | 512 | 400 | 312 | 320 | 184 | 256 |
| 79 | 84 | 544 | 232 | 288 | 1216 | 2880 | | | | | |
| 80 | 84 | 472 | 440 | | | | | | | | |
| 82 | 84 | 112 | | | | | | | | | |
| 83 | 84 | 232 | 88 | 224 | 168 | 120 | 112 | 184 | 120 | 216 | 128 |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 84 | 84 | 88 | 112 | 88 | 104 | 88 | 96 | 160 | 112 | 80 | 88 |
| 85 | 84 | 320 | 264 | 296 | 336 | 376 | 376 | 232 | 328 | 272 | |
| 88 | 84 | 240 | | | | | | | | | |
| 160 | 84 | 280 | 1144 | 471 | 126 | 304 | 232 | 207 | 352 | 120 | 280 |
| 222 | 84 | 376 | | | | | | | | | |
| 32 | 85 | 472 | 288 | 352 | 360 | 424 | 328 | 1312 | 984 | | |
| 65 | 85 | 296 | 280 | | | | | | | | |
| 66 | 85 | 376 | 432 | 520 | 464 | | | | | | |
| 68 | 85 | 497 | 216 | 256 | 232 | | | | | | |
| 69 | 85 | 600 | | | | | | | | | |
| 70 | 85 | 287 | 264 | 224 | 312 | 240 | 176 | | | | |
| 71 | 85 | 520 | | | | | | | | | |
| 74 | 85 | 257 | | | | | | | | | |
| 77 | 85 | 328 | 568 | | | | | | | | |
| 79 | 85 | 264 | 264 | 304 | 344 | 288 | 359 | 265 | 464 | 288 | 288 |
| 80 | 85 | 1632 | 4200 | 416 | | | | | | | |
| 81 | 85 | 368 | 328 | | | | | | | | |
| 82 | 85 | 568 | 320 | | | | | | | | |
| 83 | 85 | 264 | 208 | 304 | | | | | | | |
| 84 | 85 | 320 | 280 | 544 | | | | | | | |
| 85 | 85 | 63 | 96 | 96 | 96 | 73 | 120 | 88 | 120 | 80 | 120 |
| 32 | 86 | 7847 | | | | | | | | | |
| 65 | 86 | 232 | 208 | 216 | 257 | | | | | | |
| 69 | 86 | 144 | 264 | | | | | | | | |
| 73 | 86 | 304 | 416 | 360 | 328 | 360 | 351 | | | | |
| 76 | 86 | 376 | 384 | 424 | | | | | | | |
| 78 | 86 | 288 | 288 | 328 | 352 | 288 | 352 | 296 | 352 | 328 | 344 |
| 79 | 86 | 544 | 392 | 392 | 416 | 400 | 368 | 368 | | | |
| 86 | 86 | 96 | 88 | 96 | 96 | 112 | 112 | 72 | 112 | 88 | 64 |
| 8 | 87 | 1968 | | | | | | | | | |
| 32 | 87 | 264 | 224 | 888 | 912 | 240 | 184 | 1024 | 368 | 1200 | |
| 69 | 87 | 488 | 520 | 496 | 520 | 512 | 272 | | | | |
| 79 | 87 | 400 | 400 | 304 | 760 | 392 | 473 | | | | |
| 82 | 87 | 320 | | | | | | | | | |
| 84 | 87 | 728 | | | | | | | | | |
| 87 | 87 | 96 | 64 | 88 | 72 | 72 | 95 | 80 | 120 | 136 | 144 |
| 160 | 87 | 208 | 240 | 512 | 208 | 209 | | | | | |
| 69 | 88 | 304 | 304 | | | | | | | | |
| 88 | 88 | 144 | 144 | | | | | | | | |
| 32 | 89 | 2264 | 840 | 3048 | 417 | 640 | 279 | | | | |
| 65 | 89 | 264 | 232 | 288 | 352 | 463 | | | | | |
| 69 | 89 | 496 | 288 | | | | | | | | |
| 71 | 89 | 280 | | | | | | | | | |
| 75 | 89 | 336 | 495 | | | | | | | | |
| 76 | 89 | 448 | 480 | 416 | 656 | 464 | 688 | 616 | 392 | 479 | |
| 78 | 89 | 416 | 312 | | | | | | | | |
| 82 | 89 | 512 | | | | | | | | | |
| 84 | 89 | 184 | 168 | 232 | | | | | | | |
| 85 | 89 | 320 | | | | | | | | | |
| 89 | 89 | 96 | 112 | 112 | 96 | 96 | 88 | 48 | 72 | 95 | 112 |
| 160 | 89 | 208 | 647 | | | | | | | | |
| 8 | 160 | 1096 | 248 | 312 | | | | | | | |
| 13 | 160 | 2192 | 57557 | 7586 | 1887 | 2136 | 18415 | 6183 | 68748 | 18455 | 2095 |
| 32 | 160 | 240 | 864 | 3096 | 200 | 328 | 1192 | 208 | 448 | 288 | 632 |
| 37 | 160 | 7224 | | | | | | | | | |
| 49 | 160 | 919 | | | | | | | | | |
| 50 | 160 | 1120 | | | | | | | | | |
| 84 | 160 | 3760 | | | | | | | | | |
| 89 | 160 | 1048 | 4512 | | | | | | | | |
| 160 | 160 | 376 | 392 | 424 | 368 | 384 | 304 | 360 | 288 | 480 | 288 |
| 160 | 186 | 232 | 320 | 1080 | 208 | | | | | | |
| 186 | 186 | 88 | 104 | 80 | 96 | | | | | | |
| 84 | 187 | 840 | | | | | | | | | |
| 187 | 187 | 152 | | | | | | | | | |
| 65 | 188 | 4112 | | | | | | | | | |
| 69 | 188 | 4567 | | | | | | | | | |
| 71 | 188 | 4496 | | | | | | | | | |
| 72 | 188 | 4720 | | | | | | | | | |
| 78 | 188 | 2888 | | | | | | | | | |
| 82 | 188 | 4272 | | | | | | | | | |
| 83 | 188 | 3016 | 648 | 2528 | 6096 | | | | | | |
| 89 | 188 | 4760 | | | | | | | | | |
| 188 | 188 | 72 | 80 | 72 | 72 | 72 | 32 | 72 | 72 | 64 | 80 |
| 32 | 189 | 497 | 1416 | | | | | | | | |
| 69 | 189 | 1072 | | | | | | | | | |

APPENDIX A-continued

Entries 395
Serial 1234

| First Key Press | Second Key Press | TS1 | TS2 | TS3 | TS4 | TS5 | TS6 | TS7 | TS8 | TS9 | TS10 |
|---|---|---|---|---|---|---|---|---|---|---|---|
| 87 | 189 | 560 | | | | | | | | | |
| 189 | 189 | 88 | 96 | 95 | 88 | | | | | | |
| 8 | 190 | 777 | | | | | | | | | |
| 65 | 190 | 1280 | | | | | | | | | |
| 69 | 190 | 2632 | | | | | | | | | |
| 70 | 190 | 3512 | | | | | | | | | |
| 71 | 190 | 18647 | | | | | | | | | |
| 75 | 190 | 4576 | | | | | | | | | |
| 78 | 190 | 3824 | 3375 | 18175 | | | | | | | |
| 82 | 190 | 3096 | | | | | | | | | |
| 83 | 190 | 9464 | 1832 | 3144 | 2352 | 1088 | | | | | |
| 84 | 190 | 3032 | 58061 | | | | | | | | |
| 89 | 190 | 3391 | | | | | | | | | |
| 190 | 190 | 96 | 64 | 71 | 64 | 72 | 72 | 72 | 64 | 80 | 96 |
| 160 | 191 | 839 | | | | | | | | | |
| 191 | 191 | 88 | | | | | | | | | |
| 78 | 222 | 632 | 608 | | | | | | | | |
| 84 | 222 | 5655 | 792 | | | | | | | | |
| 222 | 222 | 104 | 104 | 72 | 88 | | | | | | |

APPENDIX B

June 26 1:16 pm
The Road to Newness
From Eureka Moment To Market: Bringing Ideas To Fruition
The rise of the World Wide Web in the 1990s heralded an age of innovation, enabling us to make nearly every kind of interaction better, cheaper and faster.
Investors have been rewarded for funding big, game-changing ideas during this era. Yet many of these innovations have been relatively modest concepts. Being first has been key: Test your idea, fail early and pivot until you have arrived at something that captures the popular imagination.
That's no longer the case. With so much reward for low-risk ventures, fewer entities are drawn to risky investments into the unknown. But what are the subsets of creativity, and how much risk is involved in each today?
Science is the riskiest investment. The federal government has long been a consistent source of funding for scientific research, but now Congress is scaling back. Corporations can't afford to make investments that many take years, if not decades, to pay off. So science funding has become the responsibility of nonprofits, universities and a handful of extremely rich companies.
Invention is only slightly less risky than science. Inventions can sit on shelves for years until someone figures out how to use them to solve a problem in a way that consumers will buy. While there are more corporations that spend money on invention than invest in science, it is carefully controlled spending.
Innovation is the game of choice for those who want to see a quick return on their investment. Tweaking an invention to produce yet another popular product can be done so quickly that we are now in an innovation loop that no longer relies on completely new inventions to produce ever more wealth for investors. It's a spinning wheel that no longer pauses.
The glamour of innovation so outshines invention these days that inventor support groups have sprung up to champion these maligned but essential players. The Maker Movement—young inventors using inexpensive technology to make prototypes without the benefit of outside funding or the blessing of established authorities—is reinvigorating the reputation of invention.
End 2:02 pm

The invention claimed is:

1. A system for continuous monitoring of central nervous system diseases, comprising:
   a computing device having a keyboard and a typing cadence detector that:
     detects a plurality of pieces of key event data generated from continuous typing of a document, the key event data generated during a sub-clinical typing activity and having a plurality of key combinations and one or more pieces of timing data about presses of the plurality of key combinations during a continuous typing sequence that describes a cadence of typing of keys on the keyboard; and
     secures the key event data by removing an original clock stamp from each piece of key event data, and generates a plurality of pieces of typing cadence data from the secured key event data, the typing cadence data comprising time differentials between key press and key release actions determined from at least one of clock time data and one or more pieces of timing data for the plurality of pieces of key event data; and
   a continuous monitoring apparatus having a processor that executes a plurality of lines of computer code so that the processor is configured to:
     receive the plurality of pieces of typing cadence data for a particular patient at different times;
     process the typing cadence data to generate a consistency measure by a coefficient of variance process;
     generate data about a neurological disorder of a user using the generated consistency measure; and
     generate a chart displaying the consistency measure of the user having the neurological disorder, the consistency measure of a second user that does not have a neurological disorder and an indicator showing a progress of the neurological disorder of the user.

2. The system of claim 1, wherein the computing device is capable of displaying the generated chart for the user.

3. The system of claim 2, wherein the user is one of a doctor and the patient.

4. The system of claim 1, wherein the processor is further configured to generate an updated data report each time new typing cadence data for the patient is received.

5. A method for continuous monitoring of central nervous system diseases, comprising:
- detecting, by a typing cadence detector located in a computer system having a keyboard, a plurality of pieces of key event data generated from continuous typing of a document, the key event data generated during a sub-clinical typing activity and having a plurality of key combinations and one or more pieces of timing data about presses of the plurality of key combinations during a continuous typing sequence that describes a cadence of typing of keys on the keyboard, securing the key event data by removing an original clock stamp from each piece of key event data and generating a plurality of pieces of typing cadence data based on the cadence of typing of keys, the typing cadence data comprising time differentials between key press and key release actions determined from at least one of clock time data and one or more pieces of timing data for the plurality of pieces of key event data;
- receiving, at a continuous monitoring apparatus, the plurality of pieces of typing cadence data for a particular patient at different times; and
- processing the typing cadence data to generate a consistency measure by a coefficient of variance process;
- generating data using the generated consistency measure about a neurological disorder of a user; and
- generating a chart displaying the consistency measure of the user having the neurological disorder, the consistency measure of a second user that does not have a neurological disorder and an indicator showing a progress of the neurological disorder of the user.

6. The method of claim 5 further comprising displaying, on the computing device, the generated chart for the user.

7. The method of claim 6, wherein the user is one of a doctor and the patient.

8. The method of claim 5, wherein generating the chart further comprises generating an updated chart each time new typing cadence data for the user is received.

9. The system of claim 1, wherein the typing cadence data is a timing of a plurality of key presses of the keyboard during a time period.

10. The method of claim 5, wherein the typing cadence data is a timing of a plurality of key presses of the keyboard during a time period.

11. The system of claim 1, wherein the time differentials include a dwell time describing a time difference between a key press of a key and a release of the key by the user and a flight time describing a time difference between a key press of a first key and a key press of a second key.

12. The method of claim 5, wherein the time differentials include a dwell time describing a time difference between a key press of a key and a release of the key by the user and a flight time describing a time difference between a key press of a first key and a key press of a second key.

* * * * *